(12) United States Patent
Karalkar et al.

(10) Patent No.: US 11,850,258 B1
(45) Date of Patent: Dec. 26, 2023

(54) RIBONUCLEOSIDE DERIVATIVES WITH 3'-AMINOXY GROUPS

(71) Applicants: Nilesh B. Karalkar, Gainesville, FL (US); Steven A. Benner, Gainesville, FL (US)

(72) Inventors: Nilesh B. Karalkar, Gainesville, FL (US); Steven A. Benner, Gainesville, FL (US)

( * ) Notice: Subject to any disclaimer, the term of this patent is extended or adjusted under 35 U.S.C. 154(b) by 339 days.

(21) Appl. No.: 16/887,951

(22) Filed: May 29, 2020

(51) Int. Cl.
*A61K 31/708* (2006.01)
*C12P 19/34* (2006.01)
*A61K 31/7072* (2006.01)
*A61K 31/7068* (2006.01)
*A61K 31/7076* (2006.01)

(52) U.S. Cl.
CPC ........ *A61K 31/708* (2013.01); *A61K 31/7068* (2013.01); *A61K 31/7072* (2013.01); *A61K 31/7076* (2013.01); *C12P 19/34* (2013.01)

(58) Field of Classification Search
CPC ......... C07H 9/067; C07H 19/167; C07H 7/06
See application file for complete search history.

(56) References Cited

U.S. PATENT DOCUMENTS

2019/0144905 A1* 5/2019 Chen ...................... C07H 19/04
435/91.5

FOREIGN PATENT DOCUMENTS

WO   WO2013192078 A1 * 12/2013

* cited by examiner

*Primary Examiner* — Bahar Craigo

(57) ABSTRACT

This invention claims ribonucleosides and their derivatives, including triphosphates, that have a 3'-$ONH_2$ moiety instead of a 3'-OH moiety.

19 Claims, 11 Drawing Sheets

RIBONUCLEOSIDE DERIVATIVES WITH 3'-AMINOXY GROUPS

STATEMENT OF RIGHTS TO INVENTIONS MADE UNDER FEDERALLY-SPONSORED RESEARCH

Figure 1:
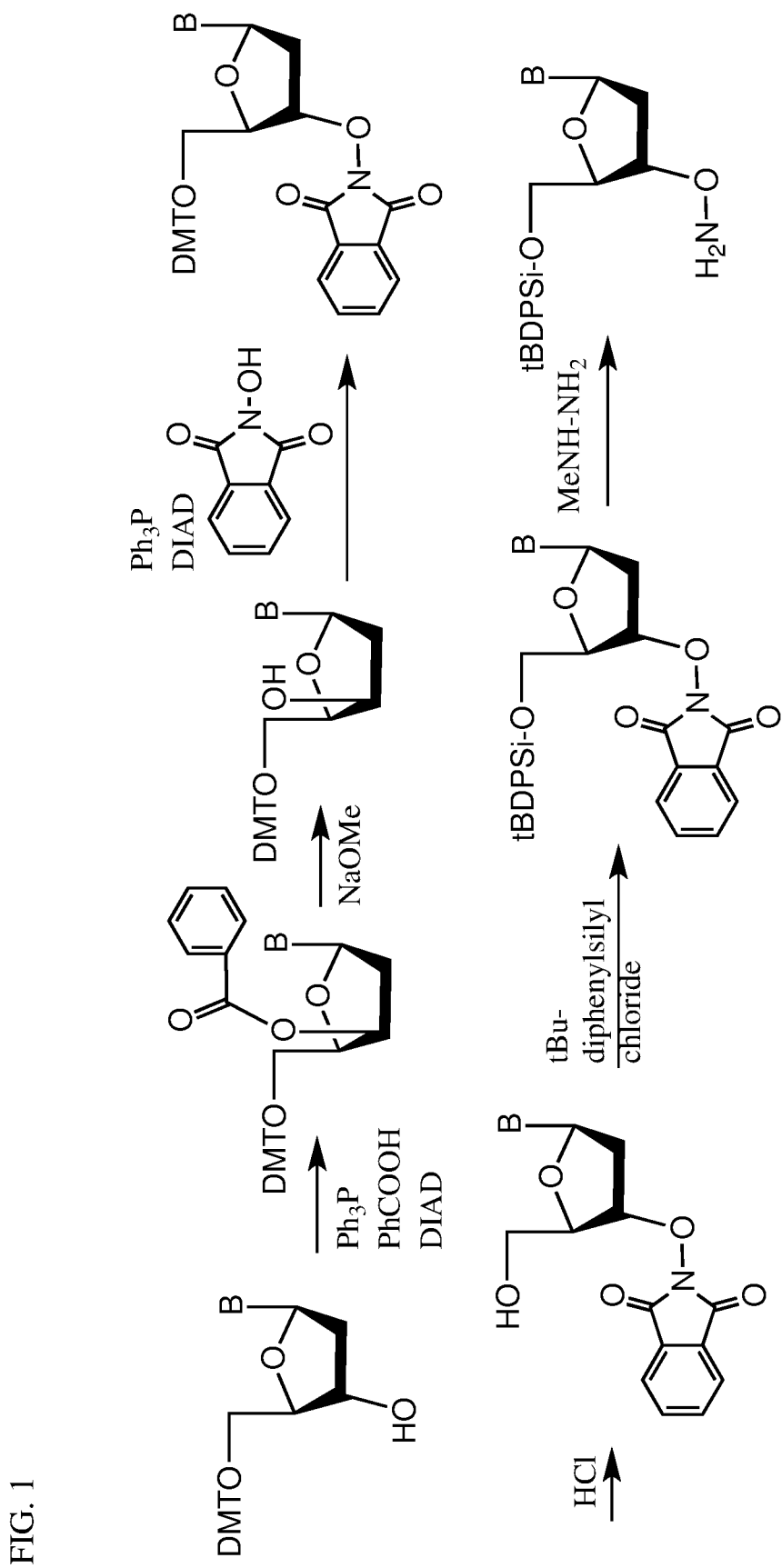

This work was supported by the National Institute of General Medical Science of the National Institutes of Health under Award Numbers R42GM119494 and R41GM115130. The government has certain rights in the invention.

CROSS REFERENCE TO RELATED APPLICATIONS

None

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

This invention relates to the field of nucleic acids, more specifically to ribonucleosides, their analogs, and their derivatives whose 3'-oxygen atoms are covalently bonded to a moiety that is stable under standard conditions where oligonucleotides are used, but can be removed by mild chemical treatments. Still more specifically, this invention relates to ribonucleosides and their derivatives where their 3'-oxygen is bonded to a nitrogen atom. Such derivatives are said to have an "aminoxy" group. Still more specifically, this invention claims ribonucleoside analogs and derivatives that have aminoxy groups, processes for synthesizing them, and useful compositions that comprise them.

(2) Description of Related Art

The art contains enzymatic processes by which a single 2'-deoxyribonucleotide derivative is added to a DNA oligonucleotide (a "primer"), without immediate further extension. The initial enzymatic extension is done in either a templated fashion or an untemplated fashion. The first is often done using a DNA polymerase, an RNA polymerase, or a reverse transcriptase [Benner, S. A., Hutter, D., Leal, N. A., Chen, F. (2011) Reagents for Reversibly Terminating Primer extension. U.S. Pat. No. 8,034,923][Benner, S. A., Hutter, D., Leal, N. A. (2012) Reagents for Reversibly Terminating Primer Extension. U.S. Pat. No. 8,212,020]. The second is often done using a terminal DNA transferase [Benner, S. A., Leal, N. A. (2017) Processes with Terminal Transferase, Aminoxy Nucleoside Triphosphates, and Nucleobase Analogs. U.S. patent Ser. No. 10/654,841] or a polymerase able to do untemplated extension, such as polymerase theta [Thomas, C., Rusanov, T., Hoang, T., Augustin, T., Kent, T., Gaspar, I., & Pomerantz, R. T. (2019). One-step enzymatic modification of RNA 3' termini using polymerase θ. *Nucleic Acids Research* 47, 3272-3283]. In either case, the enzyme requires, in addition to the primer itself, a 2'-deoxyribonucleoside triphosphate where its 3'-oxygen carries a substituent other than hydrogen, the natural substituent. Instead of this hydrogen, the 3'-oxygen may have, for example, a moiety such as a methyl group, which prevents a second nucleotide to be added to the primer after the first is added. Primer extension is said to be "terminated".

Of special utility are 3'-O blocking moieties that can later be removed under mild conditions. Such processes, if repeated cyclically, are said to involve "reversible termination". Widely used in the art for reversible termination are 3'-O azidomethyl moieties and 3'-O-amino moieties. After the enzyme has added a single nucleotide, the primer has gained a nucleotide with respectively a 3'-O-azidomethyl moiety or a 3'-O amino-moiety, which is then removed by, respectively, a phosphine or buffered sodium nitrite, for example. The unblocked extended primer now has a free 3'-OH group, and can be extended again. The cycle may be repeated.

Reversible termination is widely used for both DNA sequencing and DNA synthesis. In the first case, where the triphosphate is either tagged or untagged, the pause after the single nucleotide template-directed addition gives the process time to determine which nucleotide was added and, from this information, to infer the nucleotide in the template that it was added opposite to. For DNA synthesis, termination gives the process time to wash away the reagents, including the triphosphates, that were used to make the first addition of a known nucleotide, and to prepare to deliver the reagents needed to add the following nucleotide. Both of these processes have enormous utility.

A long-standing problem relates to efforts to adapt analogous processes to the synthesis of RNA. RNA is much more expensive to synthesize chemically than DNA, making enzymatic and non-enzymatic processes long sought. All efforts have encountered the well-known fact that RNA is a very different molecule from DNA. Ribonucleic acid has a 2'-hydroxyl group as well as a 3'-hydroxyl group. This additional hydroxyl group makes phosphoramidite-based chemical synthesis of RNA considerably more difficult and expensive than phosphoramidite-based chemical synthesis of DNA. Further, this 2'-hydroxyl group makes the RNA after synthesis easily degraded under alkaline conditions, alkaline conditions that are commonly used to remove protecting groups from the nucleobases. This protection is necessary using standard phosphoramidite chemistry.

For these reasons, processes that use 3'-O-aminoxy protection for the enzymatic synthesis of RNA have long been specifically desired. Unfortunately, the required nucleoside triphosphates having a 3'-O amino group have not been available. As disclosed below, numerous attempts to make these compounds using guidance from the art have all failed.

BRIEF SUMMARY OF THE INVENTION

This invention delivers previously unknown ribonucleoside derivatives having a 3'-$ONH_2$ unit, based on the invention of synthetic routes to make these. The disclosure reports processes that generate ribonucleosides and ribonucleoside triphosphates having a 3'-$ONH_2$ moiety. This makes available, for the first time, compositions of matter that have utility for the enzymatic synthesis of oligomeric RNA. Such 3'-O-amino blocked ribonucleosides have other uses as well, including being able to be captured via their reaction with aldehydes and ketones to form oximes. Further, this invention covers aqueous compositions of triphosphates that contain no hydroxylamine. Further, this invention discloses compositions that comprise aqueous solutions containing the nucleosides and their phosphorylated derivatives.

BRIEF DESCRIPTION OF THE SEVERAL VIEWS OF THE DRAWING(S)

FIG. 1. Schematic showing a process to synthesize 2'-deoxynucleosides with 3'-$ONH_2$ moieties, adapted from [Hutter, D., Kim, M. J., Karalkar, N., Leal, N., Chen, F., Guggenheim, E., Visalakski, V., Olejnik, J., Gordon, S., Benner, S. A. (2010) Labeled nucleoside triphosphates with reversibly terminating aminoalkoxyl groups. *Nucleosides Nucleotides Nucleic Acids* 29, 879-895]. "B" is a nucleobase or nucleobase analog that is appropriately protected.

Figure 2:
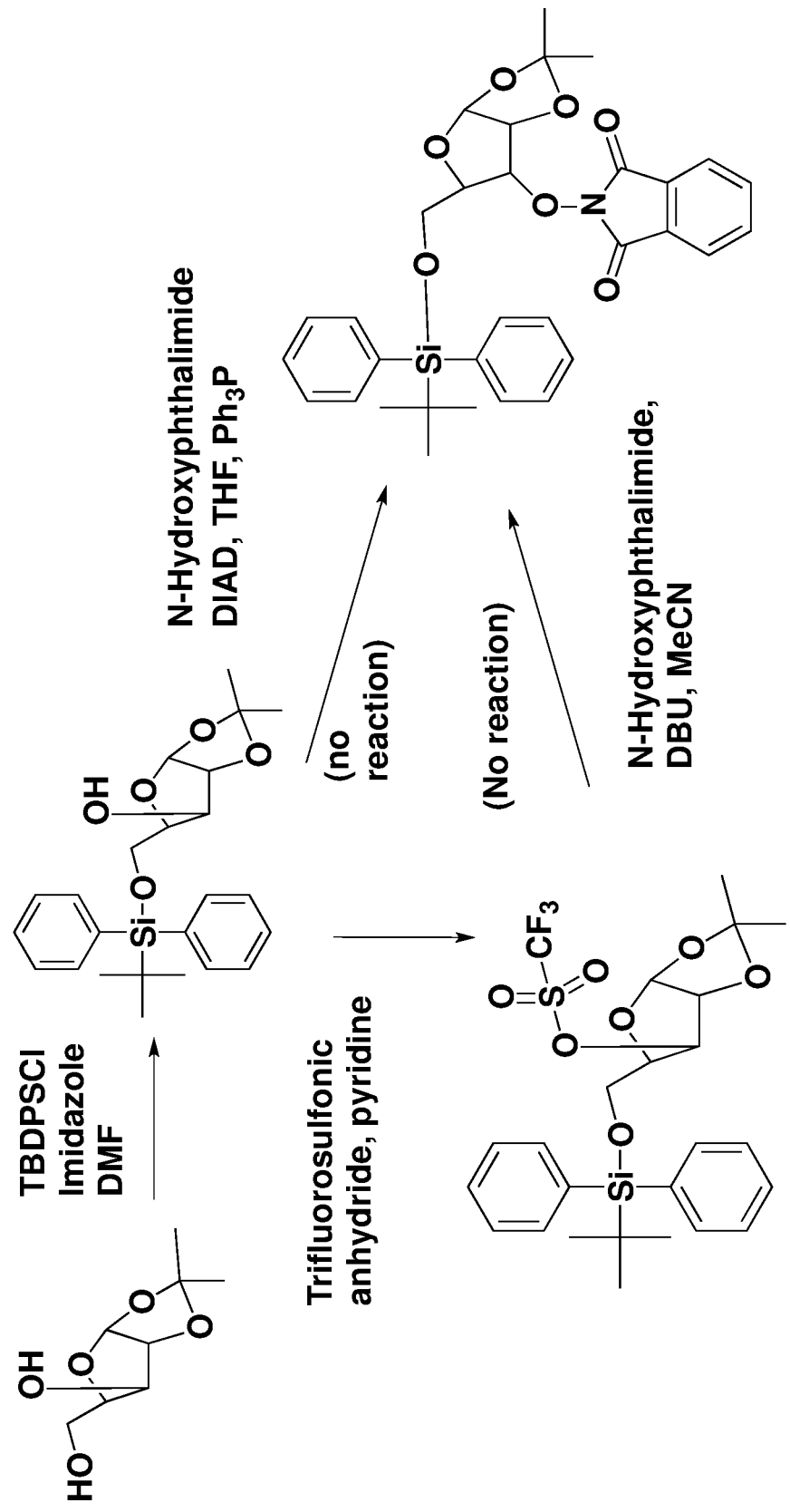

FIG. 2. Schematic showing procedures followed in attempts to make nucleoside analogs having a 3'-$ONH_2$ moiety using both a Mistunobu inversion or a standard $S_N2$ displacement. Both failed.

Figure 3:
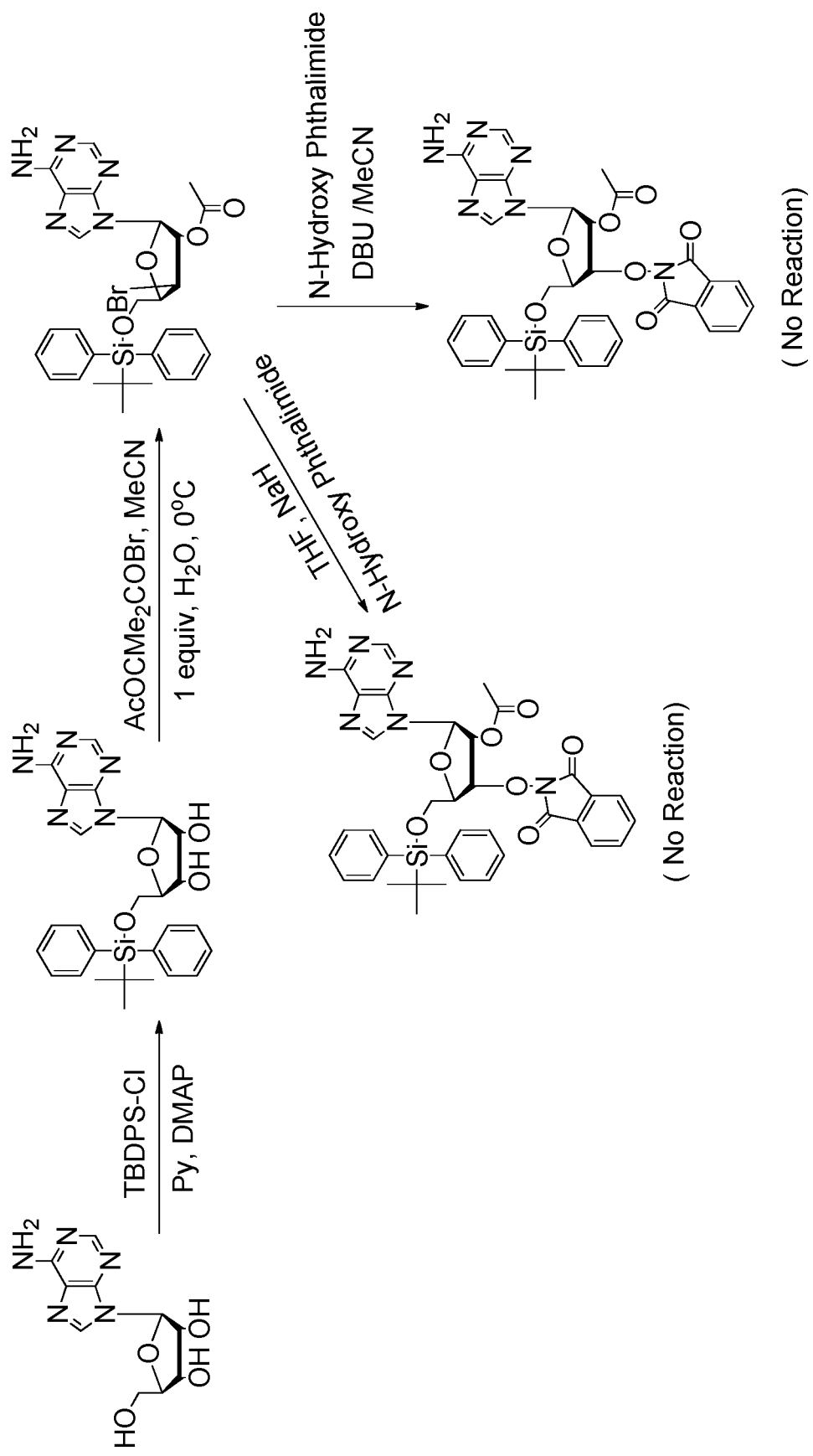

FIG. 3. Schematic showing a procedure followed in an attempt to make nucleoside analogs having a 3'-$ONH_2$ moiety. This attempt also failed.

Figure 4:
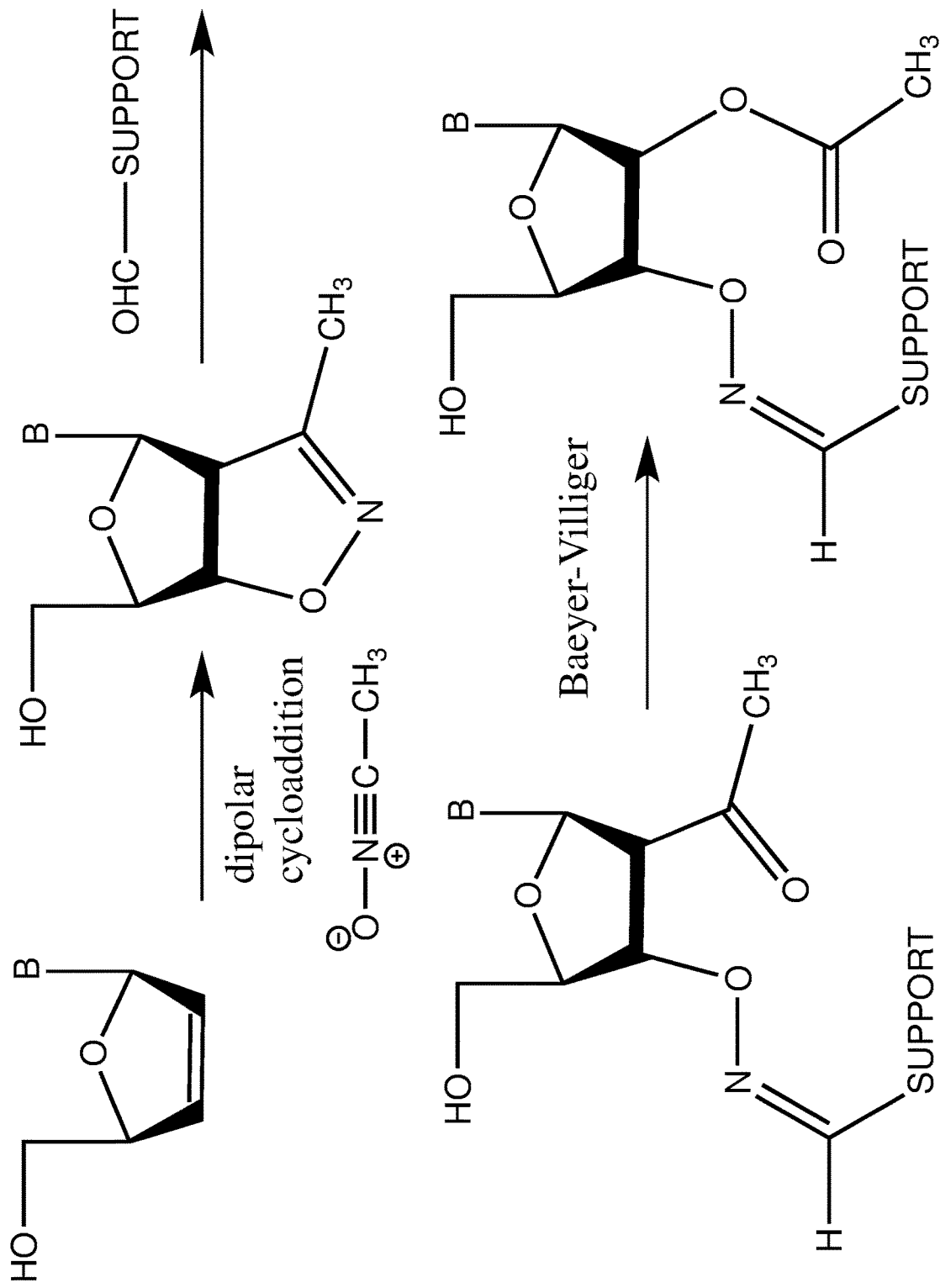

FIG. 4. Schematic showing a procedure followed in an attempt to make nucleoside analogs having a 3'-$ONH_2$ moiety. This attempt on a model system failed.

Figure 5:
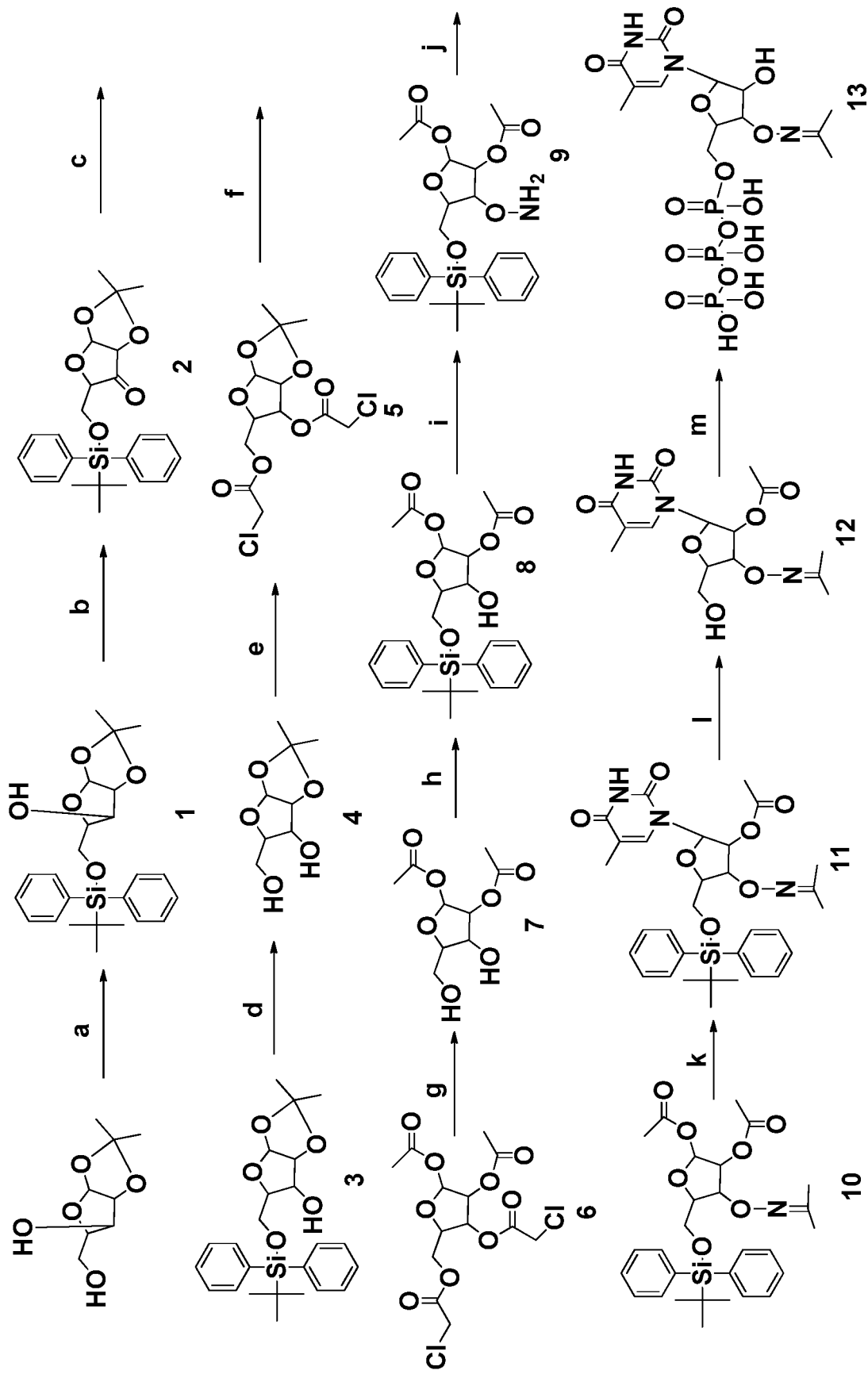

FIG. 5. Schematic showing the procedure of the instant invention for the synthesis of nucleoside triphosphate analogs having a 3'-$ONH_2$ moiety. Reagents: (a) TBDPSC1, imidazole, DMF, 0° C.; (b) PCC, $Ac_2O$, $CH_2Cl_2$, reflux (c) $NaBH_4$, EtOH, $H_2O$, 0° C.; (e) TBAF, THF, rt; (f) Chloroacetyl chloride, pyridine, ACN, 0° C.; (f) a) 85% Formic acid, 60° C., 1.5 h, b) $Ac_2O$, pyridine, DMF, rt; (g) Pyridine, MeOH, 60° C., 24 h; (h) TBDPSC1, imidazole, DMF, 0° C.; (i) MSH, NaH, ACN, rt; (j) Acetone, 1 h, rt; (k) thymine, BSA, TMS-triflate, acetonitrile, reflux, 3 h; (l) TBAF, THF, rt; (m) 2-Chloro-4H-1,3,2-benzodioxaphosphorin-4-one, Tributylammonium Pyrophosphate, $Bu_3N$, $I_2$, $NH_4OH$, rt.

Figure 6:
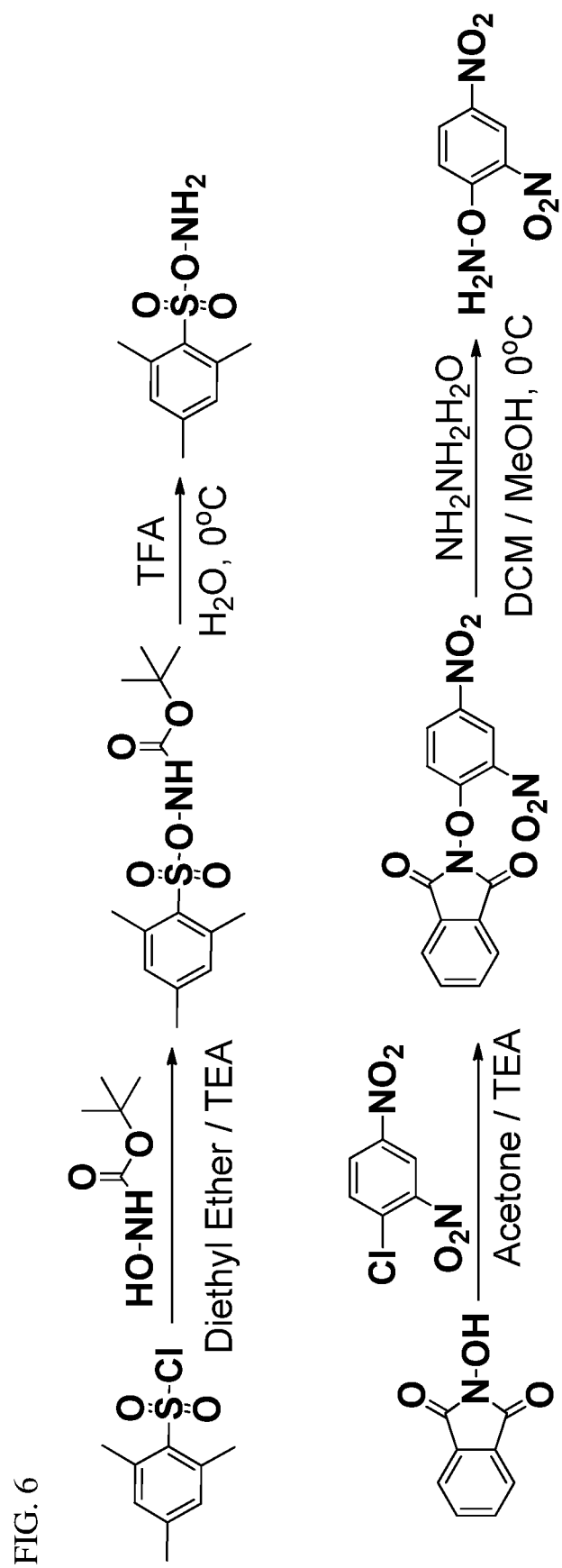

FIG. 6 Schematic showing the preparation of two reagents that were used in the process described in FIG. 6.

Figure 7:
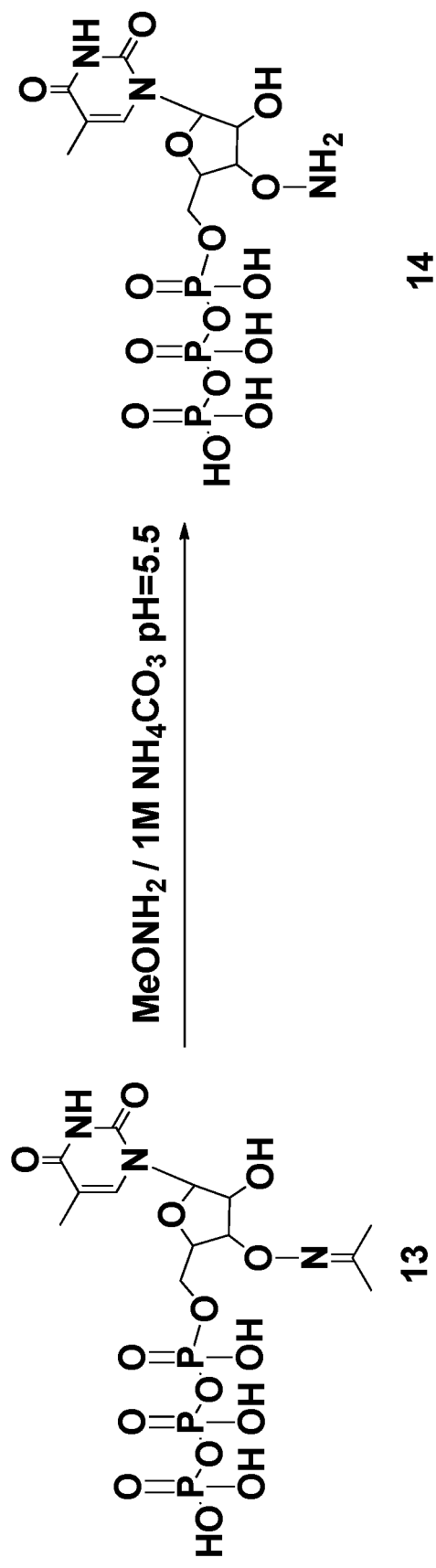

FIG. 7. Synthesis of ribonucleoside triphosphate carrying a 3'-$ONH_2$ moiety.

Figure 8:
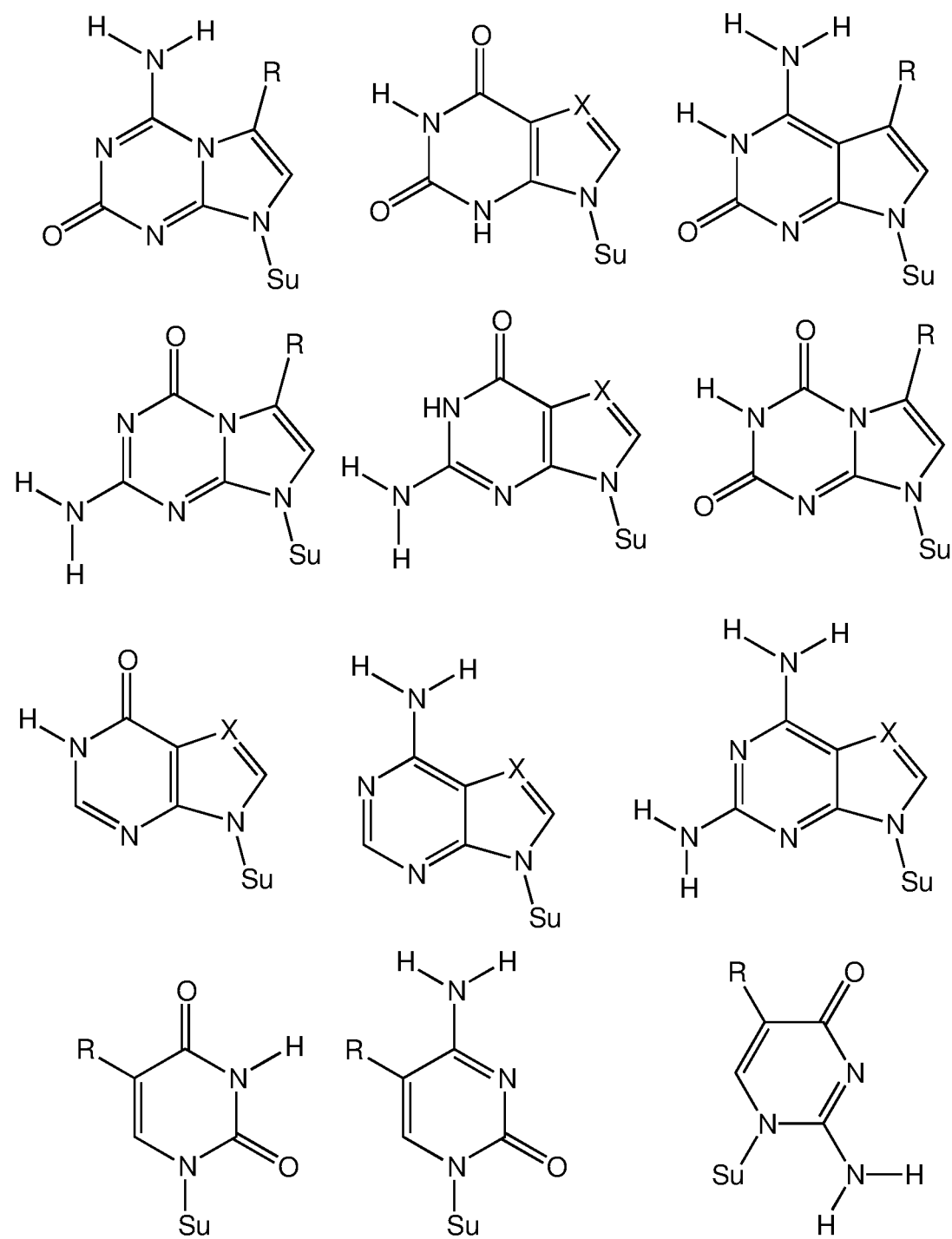

FIG. 8. By shuffling hydrogen bonding groups with a Watson-Crick geometry, a total of 6 nucleobase pairs is possible, having both size and hydrogen bonding complementarity. Different heterocyclic ring systems attached differently to the sugar implement various of these hydrogen bonding patterns. Oligonucleotides containing these nonstandard nucleotides also need to be sequenced. Therefore, 3'-$ONH_2$ moieties are also valuable.

Figure 9:
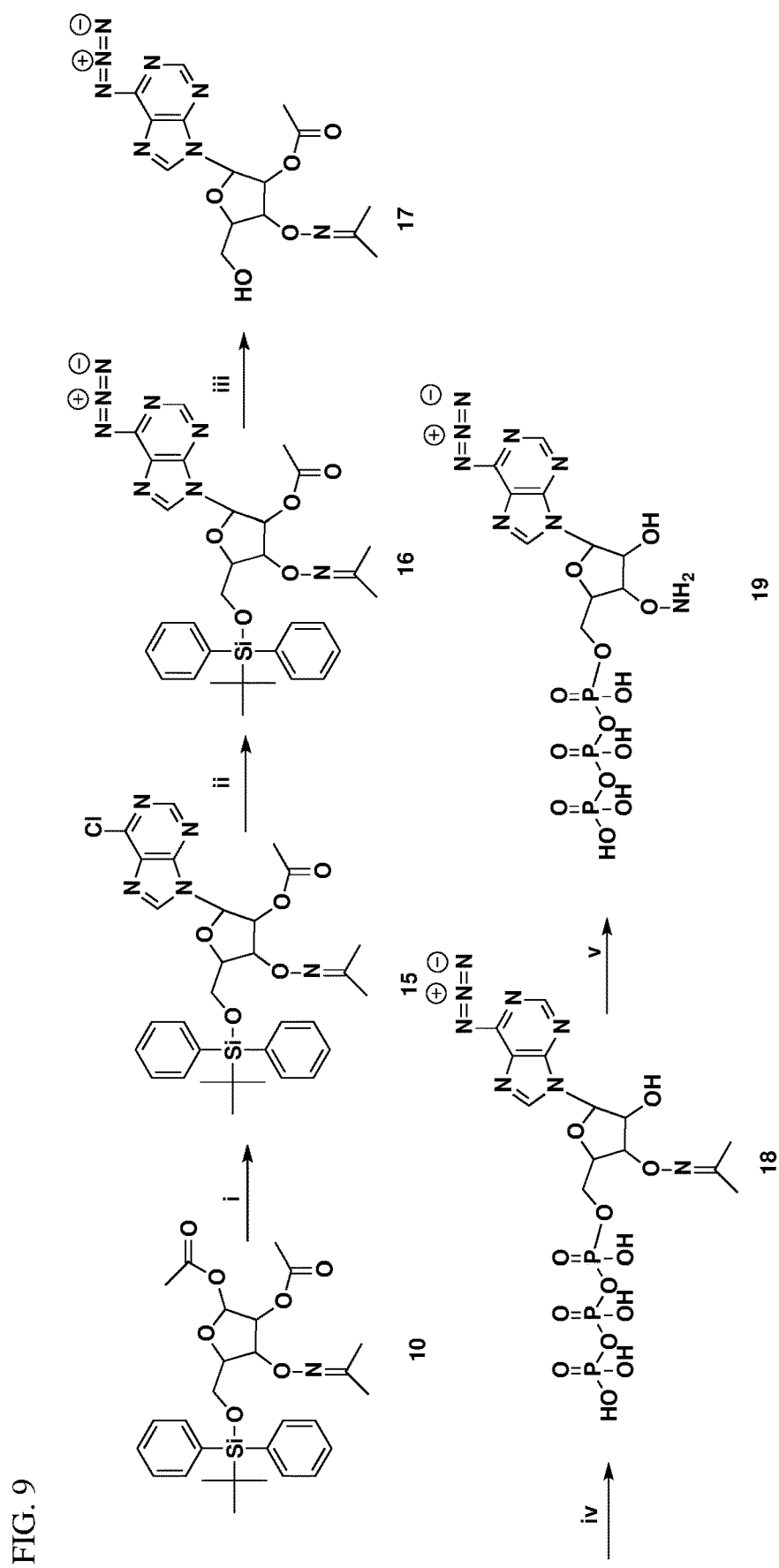

FIG. 9. Synthesis of ribonucleoside triphosphate carrying a 3'-$ONH_2$ moiety with a 6-azidopurine heterocycle. See [Chen, M. C., Mciroy, G. R. (2017) Novel use. Use of an amine masked moiety in a method of enzymatic nucleic acid synthesis. UK Patent Application GB 2568397, published 15 May 2109], the contents of which are enclosed in their entirety by this citation.

Figure 10:
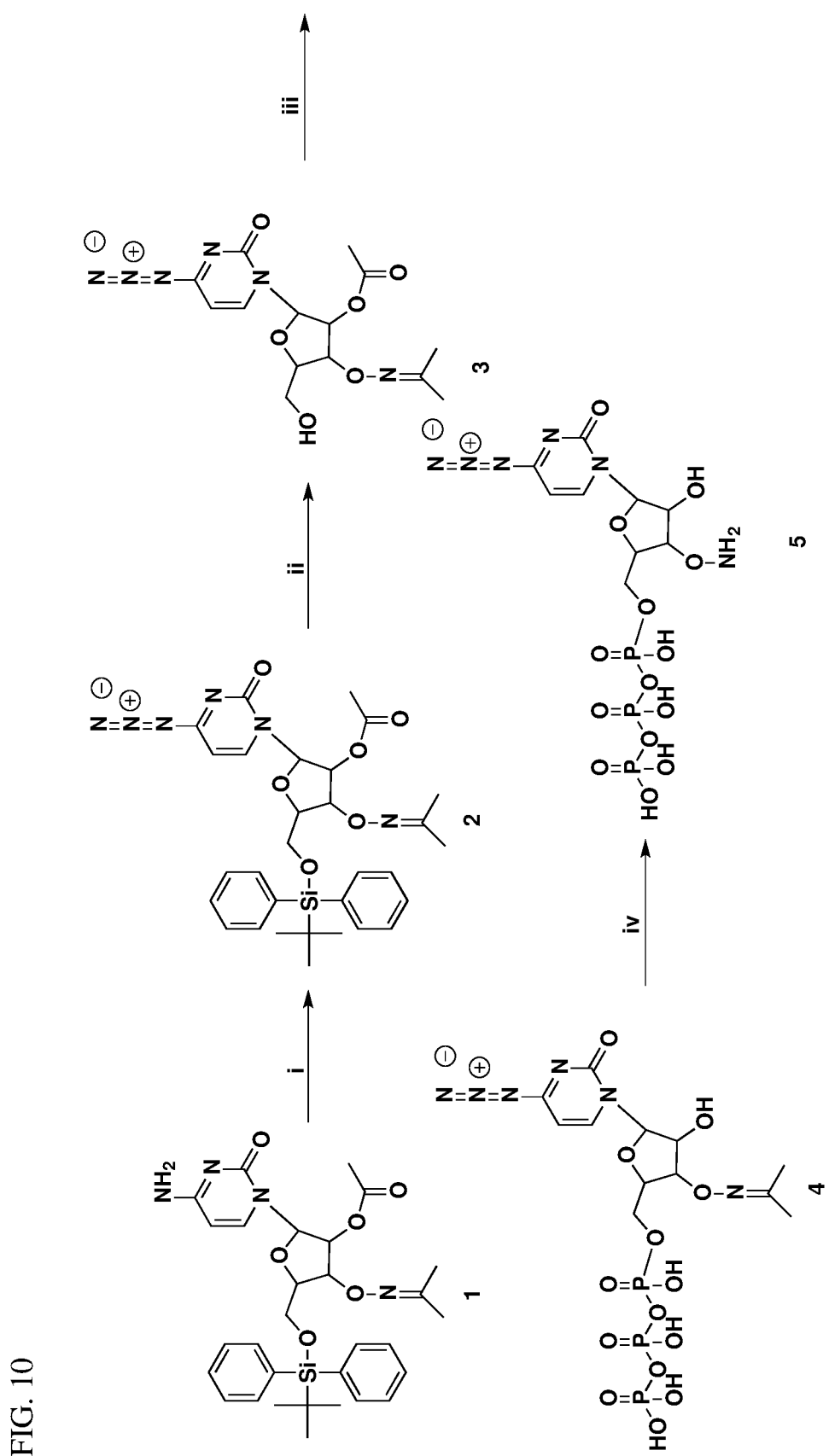

FIG. 10. Synthesis of ribonucleoside triphosphate carrying a 3'-$ONH_2$ moiety. See [Chen, M. C., Mciroy, G. R. (2017) Novel use. Use of an amine masked moiety in a method of enzymatic nucleic acid synthesis. UK Patent Application GB 2568397, published 15 May 2109], the contents of which are enclosed in their entirety by this citation.

Figure 11:
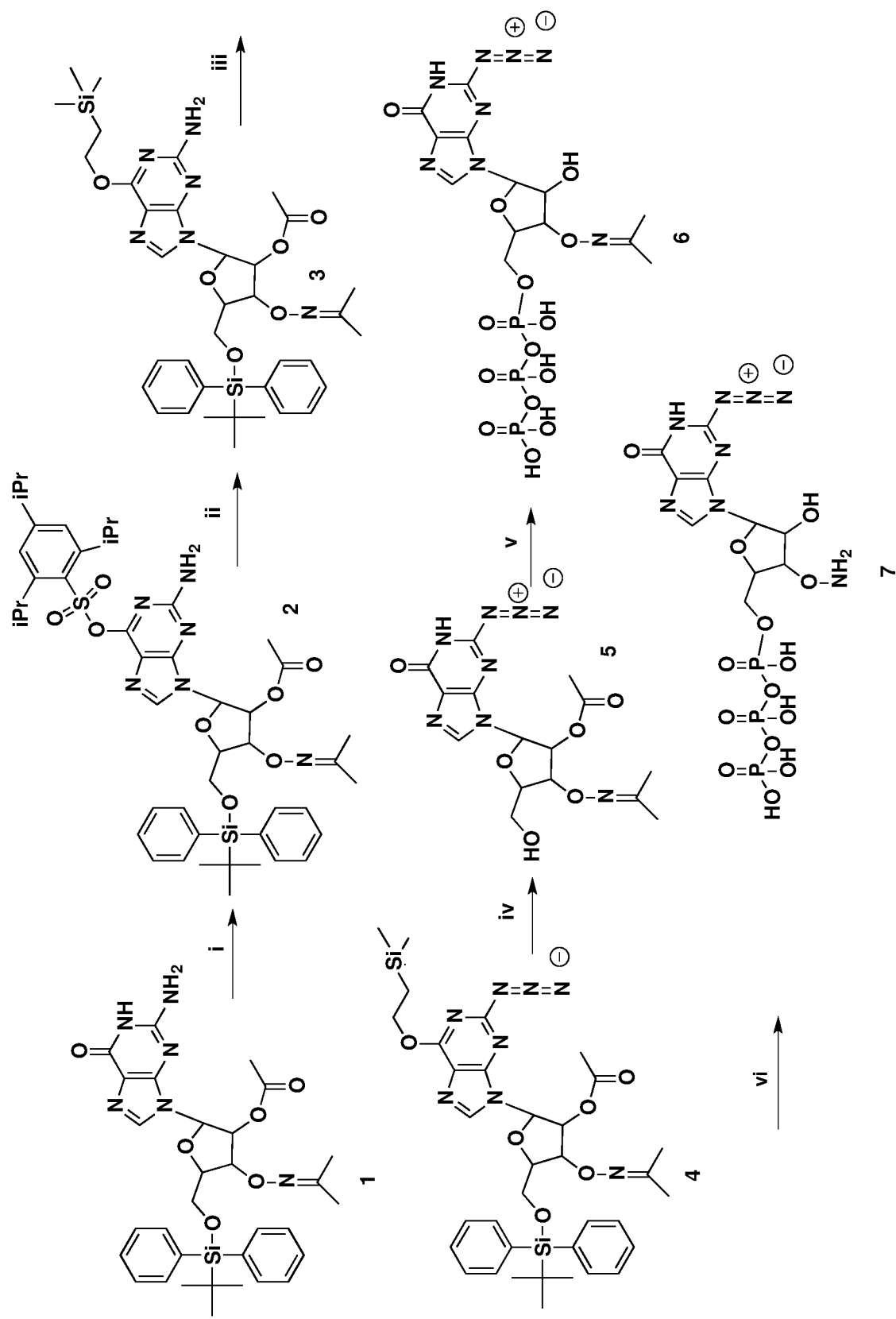

FIG. 11. Synthesis of ribonucleoside triphosphate carrying a 3'-$ONH_2$ moiety. See [Chen, M. C., Mciroy, G. R. (2017) Novel use. Use of an amine masked moiety in a method of enzymatic nucleic acid synthesis. UK Patent Application GB 2568397, published 15 May 2109], the contents of which are enclosed in their entirety by this citation.

DETAILED DESCRIPTION OF THE INVENTION

FIG. 1 shows a process from the art to synthesize 2'-deoxyribonucleoside derivatives having 3'-O-amino moiety. These derivatives are synthetic precursors to synthesize various other 2'-deoxyribonucleoside derivatives and their analogs that have utility in DNA chemistry.

The first step uses a Mitsunobu-type reaction, where diisopropylazodicarboxylate (DIAD) and triphenylphosphine ($Ph_3P$) activate the unprotected alcohol of a 2'-deoxyribonucleoside (with various protecting groups) to initiate attack of a benzoate oxygen to invert the stereochemistry at carbon-3'. This yields the benzoate derivative. After hydrolysis of the benzoate group, the stereochemistry at the 3'-hydroxyl group is inverted again with a second Mitsunobu reaction, here to initiate attack of the oxygen of N-hydroxyphathalimide to give the phalimido derivative. This derivative is a protected version of the 2'-deoxy-3'-O-amino nucleoside, and the aminoxy group can be released by treatment with methyl hydrazine, for example.

This art suggested that the 3'-O—$NH_2$ ribonucleosides might also be prepared in adapted schemes using Mitsunobu inversion sequences. One of these schemes is shown in FIG. 2. As disclosed in Example 1, this reaction failed. As an alternative, a direct $S_N2$ displacement of a trifluoromethanesulfonate derivative was attempted (FIG. 2). This also failed. FIG. 3 shows yet another attempted synthesis. It also fails.

While not wishing to be bound by theory, these multiple failures are consistent with a model that remarks on the degree to which the hydroxyl group that was hope to react is sterically hindered in the ribose molecule. This hindrance is not as severe in the 2'-deoxyribose analog. Thus, the prior art does not offer a solution to the problem of how to synthesize the ribonucleoside derivatives of the instant invention.

Therefore, an alternative route following an alternative strategy was considered (FIG. 4). Exploratory work with a model lacking the base and a hydroxymethyl side chain found that the dipolar cycloaddition worked. However, downstream steps in the conjectured synthetic route failed.

After extensive experimentation, a route was invented to make the desired ribonucleosides. This route is shown in FIG. 5. This route relied on the reagents prepared by the methods shown in FIG. 6.

In the presently preferred route to the 3'-O-amino derivatives of ribose of the instant invention, the acetonide of xylose was protected as the tertiary-butyl-diphenylsilyl ether. The free secondary hydroxyl group was then oxidized to give a ketone, which was then reduced to give the alcohol having the ribose stereochemistry. The silyl group was then removed, and the two hydroxyl groups were protected as the chloroacetate esters.

This strategic protection allowed the acetonide to be removed under acidic conditions. The two freed-up hydroxyl groups were then converted to their simple acetate esters. Then the chloroacetate groups were selectively removed, the primary hydroxyl group was protected as a tertiary-butyl-diphenylsilyl ether, and the amino group was directly added to the free hydroxyl group using an electrophilic sulfonate aminating reagent. This is described in Example 3.

The aminoxy group was selectively protected as its oxime with acetone. This derivative can then be directly treated with nucleobase to form the nucleotide analog. Here, stereochemistry the correct stereochemistry is ensured by participation of the 2'-acetoxy group. This material is then converted to the triphosphate using Ludwig Eckstein conditions (FIG. 7). As is well known in the art, the triphosphate is present only at low pH. In general, it is presented in the form of a salt, preferably the sodium or potassium salt, or the triethyl ammonium salt. Most preferably, the counter ion for the phosphate groups is what was most recently used in an HPLC purification.

As an alternative route to prepare the triphosphate, the aminoxy group may be uses a handle to attached the intermediate to an aldehyde or ketone attached to a solid support. Here, instead of Compound 13, the acetone is replaced by an aldehyde or ketone attached to a support as described in U.S. patent Ser. No. 10/654,841, whose disclosure is incorporate in its entirety by reference into the instant disclosure. The Ludwig Eckstein triphosphate synthesis procedure is then applied to the support directly. The triphosphate is then released from the support with an alkoxylamine, preferably methoxylamine, but not hydroxylamine. The alkoxylamine is then immediately removed by lyophilization. This allows the resulting triphosphate to contain essentially no free 3'-OH groups.

Example 3 describes this process specifically for the preparation of the uridine analog. However, the herein disclosed process of attaching a nucleoside to 2'-acetylated ribose derivatives is general for all other nucleosides as long as the glycosidic bond that is formed is a carbon-nitrogen bond. Therefore, this process can be applied to synthesize 3'-O-amino derivatives of a broad range of ribonucleoside analog. These include analogs where the hydrogen bonding pattern presented by the heterocycle to its complementary nucleobase is different from what is found in standard nucleotides. Such compounds are disclosed in the art, and the presently preferred heterocycles are shown in FIG. 8. Other unnatural heterocycles are shown in FIG. 9, FIG. 10, and FIG. 11.

Further, compositions that comprise aqueous solutions containing the nucleosides and their phosphorylated derivatives also have utility. Preferably, the aqueous solution contains a buffer. More preferably, the aqueous solution contains an enzyme, such as a DNA polymerase, RNA polymerase, reverse transcriptase, terminal transferase, or a polymerase such as polymerase theta, operating in an untemplated mode. These enzymes may also be present in these compositions in mutated form. Alternatively, the mixture may contain a template made of standard nucleotides, nucleotides with non-standard nucleobases, or universally templating nucleotides [Hoff, K., Halpain, M., Garbagnati, G., Edwards, J. S., & Zhou, W. (2020). Enzymatic Synthesis of Designer DNA Using Cyclic Reversible Termination and a Universal Template. *ACS Synthetic Biology*. doi.org/10.1021/acssynbio.9b00315].

These compositions support processes that to a primer a nucleotide analog with a 3'-O—$NH_2$ group, said process comprising contacting said primer in an aqueous solution containing an enzyme and a triphosphate of the instant invention. The enzyme is preferably a DNA polymerase, and RNA polymerase, a reverse transcriptase, or a terminal transferase.

EXAMPLES

Example 1. Unsuccessful Attempt to Make the 3'-O Aminoxy Ribonucleosides

To a solution of 1 (1.0 g, 2.3 mmol) in THF (50 mL), were added N-hydroxyphthalimide (0.665 g, 4 mmol), triphenylphosphine (1.1 g, 4 mmol). DIAD (0.78 mL, 4 mmol) was added dropwise at 0° C. The reaction was let to warm to RT overnight, and the TLC analysis showed No reaction. It was then was quenched by the addition of water (0.5 mL). The solvents were removed in vacuo to recover the starting material after column chromatography.

5'-O-[(tert-Butyl)diphenylsilyl]adenosine (1). To a suspension of adenosine (10 g, 37.45 mmol) in 186 mL of dry pyridine were added 4-(dimethylamino)pyridine (0.226 g, 1.85 mmol) and (t-Bu)$Ph_2$SiCl (11.68 mL, 45 mmol) under argon. The mixture was stirred at r.t. for 40 h. After the disappearance of the starting material (TLC), 10 ml of MeOH was added to the mixture, and the mixture was stirred at r.t. for 0.5 h. After removing the solvent, the residue was dissolved in $CHCl_3$ (50 ml) and precipitated with $Et_2O$ (200 ml) to form a white solid. After filtration, the solid was washed with $Et_2O$ and water, and dried ($P_2O_5$) to give 1 (17.0 g).

2'-O-Acetyl-3'-bromo-5'-O-[(tert-butyl) diphenylsilyl]-3'-deoxyadenosine (2). To a suspension of 1 (10 g, 20 mmol) in MeCN (200 ml) containing a trace amount of $H_2O$ (0.325 ml, 2.3 mmol) was added a soln. of 2-acetoxyisobutyryl bromide (8.75 ml, 0.06 mol) in dry MeCN (50 ml) at 0° C. over 1 h. A clear soln. was formed first after 2.5 h, and, then, a solid precipitate was formed when the reaction progressed. The mixture was stirred at 0° C. for 5 h. Sat. $NaHCO_3$ soln. was added dropwise at 0° C. until the pH of the soln. reached 8, and, then, the soln. was neutralized with AcOH to pH 5. The solid was filtered and washed with cold $H_2O$ (75 ml), MeCN (50 ml), and $Et_{2O}$ (50 ml). The solid product was dried ($P_2O_5$) to yield 3.5 g of 2.

$S_N2$ displayments were then attempted under a variety of conditions. For example, to use N-hydroxyphthalimide as a nucleophile and diazabicycloundecanne (DBU) as a base in acetonitrile (MeCN) as a solvent, intermediate 2 (0.61 g. 1 mmol) was dissolved in acetonitrile (5 mL). Then, N-hydroxyphthalimide (163 mg, 1 mmol) and DBU (0.149 mL, 1 mmol) were added. The reaction mixture was stirred at room temperature for 24 h. TLC analysis indicated that no reaction occurred. The solution was diluted with dichloromethane, and water was added. The product was extracted with dichloromethane. The organic phase was washed with water and brine, dried ($Na_2SO_4$), and concentrated. The intermediate 2 was recovered In another attempt, DBU was replaced as the base by sodium hydride (NaH). A solution of 2 (609 mg, 1 mmol) and N-hyroxyphthalimide (169 mg, 1 mmoL) in anhydrous THF (15 mL) was treated with NaH (80 mg, 2.0 mmol) under argon. The suspension was stirred at room temperature for 24 h. Again, analysis by thin layer chromatography (TLC) showed that no reaction had occurred. The solution was filtered and evaporated to dryness. The residue was dissolved in ethyl acetate (150 mL) and washed with water (20 mL), $NaHCO_3$ solution (2×25 mL), and brine (50 mL). The aqueous layer was extracted with $CHCl_3$ (3×20 mL), and the combined organic layers were dried ($Na_2SO_4$). The solvent was removed to recover the starting material.

Example 2. Unsuccessful Attempt to Make the 3'-O Aminoxy Ribonucleosides

To a solution of compound 1 (4.5 g, 14.59 mmol) in dichloromethane (150 mL) were added pyridine (5.9 mL, 73 mmol), and trifluoromethanesulfonic anhydride (5.1 mL, 30.66 mmol) at 0° C. The reaction mixture was stirred in an ice bath for 40 min. After completion of the reaction, ice-cold water was added, and the product was extracted with dichloromethane. The organic phase was washed with water and brine, dried ($Na_2SO_4$), and concentrated. The crude product 2 (6.4 g) was used for the next reaction without further purification.

The crude triflate 2 (1.0 g. 2.27 mmol) was dissolved in acetonitrile (20 mL), and N-hydroxyphthalimide (1.65 g, 10.15 mmol) and DBU (1.52 mL, 10.215 mmol) were added. The reaction mixture was stirred at room temperature for 24 h. TLC analysis indicates No reaction. The solution was diluted with dichloromethane, and water was added. The product was extracted with dichloromethane. The organic phase was washed with water and brine, dried ($Na_2SO_4$), and concentrated. Intermediate 2 was recovered.

Example 3. Successful Synthesis (FIG. 5)

Preparation of the Aminating Reagent (FIG. 6).

To a solution of 2,4,6-trimethylbenzene-1-sulfonyl chloride (25 g, 114 mmol) and tert-butyl hydroxycarbamate (15.2 g, 114 mmol) in $Et_2O$ (300 mL) at 0° C., was dropwise added $Et_3N$ (17.4 mL, 125.4 mmol). The reaction mixture was warmed to r.t. and stirred for 4 h. Water (~150 mL) was added, and the organic layer was separated, dried over anhydrous $Na_2SO_4$, filtered, concentrated. The crude product was purified by flash chromatography on silica gel using a mixture of Hexane and ethyl acetate as the eluent (20:1 to 5:1) to afford tert-butyl (mesitylsulfonyl)oxycarbamate (29 g, 92 mmol, 82%) as a white solid.

To prepare the O-aminomesitylenesulfate, tert-butyl 4-hydroxyphenethylcarbamate (10 g, 31.73 mmol) was portion wise added to trifluoroacetic acid (92 mL) at 0° C. The reaction was stirred at 0° C. for 2 h. Ice/cold water (800 mL) was added dropwise and the reaction mixture was stirred for 30 minutes. The precipitate was filtered and washed several times with water until pH ≈7. O-Mesitylenesulfonylhydroxylamine (MSH, 4.3 g, 20 mmol, 63%) was isolated as a white solid and used immediately for the next step.

For the synthesis of the phthalimide with a dinitrophenyl group, triethylamine (17.3 mL, 125 mmol) was added dropwise to a suspension of N-hydroxyphthalimide (20.2 g, 123.8 mol) in 400 mL of acetone, and the mixture was stirred at room temperature. The reaction mixture turned dark red, and the N-hydroxyphthalimide slowly dissolved. The reaction was stirred until it became a homogeneous solution (ca. 10 min). 2,4-Dinitrochlorobenzene (25.0 g, 123.8 mol) was then added in one portion, and the reaction was stirred at room temperature for 2 h. After this time, a bright yellow suspension was formed, and the reaction mixture was poured into 1 L of ice water. The precipitate was filtered and washed three times with 100 mL of cold MeOH. The solid was compressed and washed with three 100 mL portions of hexanes and dried under vacuum to afford product as an off white solid (37.0 g, 112.5 mmol, 90% yield).

For the synthesis of O-aminodinitrophenol, 2-(2,4-Dinitrophenoxy)-1H-isoindole-1,3(2H)-dione (8 g, 24.31 mmol) dissolved in 10% EtOH in DCM (300 mL) was treated with hydrazine (2.3 mL, 74.55 mmol) with stirring overnight. The mixture was adsorbed onto silica gel and purified by column chromatography on silica gel, eluting with hexane:ethyl acetate 9:1 to 1:1 to the desired product (1 g)

Synthesis of Compound 1

To a cooled solution of 1,2-O-isopropylidene-α-D-xylofuranose (39 mmol, 7.4 g) in DMF (110 mL) were added imidazole (15.6 mmol, 10.6 g) and tert-butyldiphenylsilyl chloride (46.1 mmol, 11.8 mL). After stirring at room temperature for 48 h, the reaction was quenched with $Et_2O$ (150 mL) and water (75 mL). The aqueous layer was extracted with $Et_2O$ (3×150 mL) and the combined organic layers were washed with brine (5×70 mL), dried over $Na_2SO_4$, filtered and concentrated under reduced pressure. The crude was purified by column chromatography using Hexane: Ethyl acetate (4:1 to 1:1) to obtain the desired compound 1 (17.8 g, 41.6 mmol, 107%).

Synthesis of Compound 2 (FIG. 5)

To a solution of compound 1 (75.7 mmol, 32.4 g) in $CH_2Cl_2$ (120 mL) were added pyridinium chlorochromate (PCC, 53.3 mmol, 20.0 g), $Ac_2O$ (249.81 mmol, 23.6 mL). The mixture was heated at reflux temperature for 1 h. Reaction mixture was evaporated under reduced pressure. The crude product was purified by column chromatography using hexane:ethyl acetate (2:1) to obtain the desired compound 2 (36.1 g, 84.5 mmol, 112%). 1H NMR (300 MHz, $CDCl_3$) 7.73-7.65 (m, 2H), 7.60 (m, 2H), 7.47-7.35 (m, 6H), 6.26 (d, J=4.5 Hz, 1H), 4.43 (d, J=4.5 Hz, 1H), 4.39 (s, 1H), 3.93-3.81 (m, 2H), 2.21 (d, J=4.8 Hz, 1H), 2.07 (d, J=14.0 Hz, 1H), 1.47 (s, 6H), 1.00 (s, 9H)

Synthesis of Compound 3 (FIG. 5)

To a solution of compound 2 (84.74 mmol, 36.1 g) in a mixture of EtOH/water 9/1 (487 mL/54 mL) at 0° C., was added $NaBH_4$ (254 mmol, 9.6 g) portion-wise. The reaction mixture was stirred overnight at room temperature. The reaction mixture was concentrated under reduced pressure, diluted in mixture $DCM/NH_4Cl$ (300 mL/300 mL) and stirred for 30 min. The aqueous layer was extracted with DCM (250 mL), the combined organic layers were washed with $NH_4Cl$, water and brine, then dried over $Na_2SO_4$, filtered and concentrated under reduced pressure to give the desired compound as an oil. The crude product was purified by column chromatography using hexane:ethyl acetate (1:1) to obtain the desired compound 3 (20.6 g, 48 mmol, 57%). 1H NMR (300 MHz, $CDCl_3$) 8.37-8.27 (m, 4H), 8.07-7.96 (m, 6H), 6.46 (d, J=3.7 Hz, 1H), 5.25-5.17 (m, 1H), 4.81-4.69 (m, 1H), 4.56 (d, J=3.3 Hz, 1H), 4.52-4.41 (m, 2H), 2.95 (d, J=9.9 Hz, 1H), 2.20 (s, 3H), 2.03 (s, 3H), 1.70 (s, 9H)

Synthesis of Compound 4 (FIG. 5)

To a solution of compound 3 (20.6 g, 48.13 mmol) in THF (81 mL) was added 1M TBAF (56.2 mL) and the mixture was magnetically stirred at room temperature. After 1 h the deprotection was completed and the product showed Rf 0.47 ($CH_2Cl_2$-MeOH 4:1). The solvent was evaporated and the residual slurry was applied on top of the silica gel column. Elution with hexane:ethyl acetate (4:1) then with 0-4% methanol in $CH_2Cl_2$ furnished the desired compound 4 (8.0 g, 42.10 mmol, 88%). 1H NMR (300 MHz, $CDCl_3$) 5.83 (d, J=3.8 Hz, 1H), 4.63-4.56 (m, 1H), 4.07-3.97 (m, 2H), 3.94 (br. s., 1H), 3.85 (td, J=3.1, 8.9 Hz, 1H), 3.81-3.70 (m, 1H), 2.55 (d, J=10.5 Hz, 1H), 2.12 (br. s., 1H), 1.83 (br. s., 1H), 1.58 (s, 3H), 1.38 (s, 3H)

Synthesis of Compound 5 (FIG. 5)

Compound 4 (8.0 g, 41.92 mmol) is dissolved in acetonitrile anhydrous (375 mL). The solution is cooled to 0° C. (water-ice mixture). Pyridine (5.1 mL, 63.15 mmol) is added to the reaction. Monochloroacetyl chloride (5.1 mL, 63.15 mmol) in acetonitrile (115 ml) is slowly added dropwise to the reaction mixture (3 h). The reaction is stirred overnight at room temperature. Evaporate the solution under reduced pressure in the presence of toluene (3×100 ml) and the solid product obtained is taken up in the $CH_2Cl_2$ (200 mL). After washing with a saturated solution of $NaHCO_3$ and water, the organic solution is evaporated to dryness and the syrup obtained chromatography quickly on column. Elution with hexane:ethyl acetate (4:1 to 2:1) furnished the desired compound 5 (15.2 g, 44.2 mmol, 105%). 1H NMR (300 MHz, $CDCl_3$) d=6.21 (t, J=4.0 Hz, 1H), 5.53-5.36 (m, 2H), 4.53-4.39 (m, 2H), 4.37-4.25 (m, 1H), 4.16-4.09 (m, 4H), 2.16-2.10 (m, 6H)

Synthesis of Compound 6 (FIG. 5)

A solution of 5 (4.5 g, 11.65 mmol) in 85% formic acid (107 mL) was stirred for 1.5 h at 60° C. and evaporated. The residue was dissolved in DMF (25 mL), pyridine (2.82 mL, 34.95 mmol) and $Ac_2O$ (3.85 mL, 34.95 mmol) was added to the reaction mixture. The mixture was stirred at room temperature for 16 h and evaporated. The residue was partitioned between Diethyl ether and saturated $NaHCO_3$. The organic layer was washed with brine, dried ($Na_2SO_4$), filtered, and evaporated. The residue was purified by silica gel column chromatography (DCM/MeOH) 100/3) to give 6. (5.5 g, 14.2 mmol, 122%) The NMR of the pure compound has a mixture of both the isomers.

Synthesis of Compound 7 (FIG. 5)

Compound 6 (6 g, 15.54 mmol) was dissolved in methanol (40 mL). Pyridine (20 mL) was added and the mixture was heated at 60° C. for 1 night. The reaction was cooled and then was evaporated several times in the presence of toluene to eliminate pyridine. The residue was then dried on high vacuum. The product was used in the next step without purification.

Synthesis of Compound 10 (FIG. 5)

To a cooled solution of 7 (15.54 mmol, 3.6 g) and imidazole (43.5 mmol, 2.9 g) in DMF (60 mL) was added tert-butyldiphenylsilyl chloride (20.2 mmol, 5.8 mL) in DMF (30 mL). The mixture was stirred at room temperature for 48 h. The reaction was quenched with $Et_2O$ (100 mL) and water (50 mL). The aqueous layer was extracted with $Et_2O$ (3×100 mL) and the combined organic layers were washed with brine (5×50 mL), dried over $Na_2SO_4$, filtered and concentrated under reduced pressure. The crude was purified by column chromatography using hexane:ethyl acetate (4:1 to 1:1) to obtain the desired compound 8 (10 g, 41.6 mmol, 136%). To a solution of compound 8 (4.2 mmol, 2.0 g) in acetonitrile (45 mL) NaH (1.12 g, 60% w/w, 28 mmol) was added. To this mixture was added amino-2,4,6 trimethylbenzene sulfonate (4.2 mmol, 0.9 g) portion wise. The reaction mixture was stirred for 1 h before quenching with ice water (100 mL). The mixture was extracted with ethyl acetate (200 mL) and the combined organic layers were washed with water and brine, dried over $Na_2SO_4$, filtered, and concentrated. The residue was purified by column chromatography (hexane:ethyl acetate, 300:15 to 300:60 to 4:1) on silica gel to give the desired compound 9 as an oil. To the flask containing the aminoxy compound, acetone (25 mL) was added, and the mixture was stirred for 1 h. The solvents were then removed by rotary evaporation, and the residue was dried on high vacuum. 10 (0.55 g, 25%).

1H NMR (300 MHz, $CDCl_3$) 7.74-7.66 (m, 4H), 7.46-7.33 (m, 6H), 6.20 (d, J=1.6 Hz, 1H), 5.46-5.38 (m, 1H), 5.08 (t, J=5.6 Hz, 1H), 4.33-4.23 (m, 1H), 3.97-3.71 (m, 2H), 2.14-2.08 (m, 4H), 1.95 (s, 3H), 1.89 (s, 3H), 1.82 (s, 3H), 1.12 (s, 6H)

Synthesis of Compound 11 (FIG. 5)

N,O-Bis(trimethylsilyl)acetamide (0.44 mL, 1.81 mmol) was added to a suspension of 10 (350 mg, 0.66 mmol) and thymine (101 mg, 0.8 mmol) in anhydrous acetonitrile (25 mL). The reaction mixture was refluxed for 1 h whereupon the clear solution was cooled to room temp. TMS-triflate (0.158 mL, 0.8 mmol) was added dropwise and the resulting mixture was refluxed for 3 h. The reaction mixture was then cooled to room temp. and diluted with $CH_2Cl_2$ (50 mL), washed with saturated aq. $NaHCO_3$ (2×50 mL). The combined organic phases were dried ($Na_2SO_4$), the salts were removed by filtrations, and the solvents were removed by rotary evaporation under reduced pressure. The nucleoside derivative 11 (350 mg, 0.59 mmol, 90%) as a white solid material was recovered from the resulting yellow oil by column chromatography [5% (v/v) MeOH in $CH_2Cl_2$]$^1$H NMR (300 MHz, $CDCl_3$) 9.37 (s, 1H), 7.67-7.55 (m, 4H), 7.42-7.25 (m, 6H), 6.34 (d, J=7.7 Hz, 1H), 5.27 (dd, 7.4, 5.8, 1H), 4.98 (dd, J=1.8, 5.5 Hz, 1H), 4.23 (s, 1H), 4.02 (d, J=11.6 Hz, 1H), 3.81 (d, J=11.6 Hz, 1H), 2.06 (s, 3H), 1.81 (d, 6H), 1.40 (s, 3H), 1.06 (s, 9H)

Synthesis of Compound 12 (FIG. 5)

Tetrabutylammonium fluoride (1.42 mL, 1.4 mmol, 1.0 m solution in THF) was added to a solution of 11 (700 mg, 1.18 mmol) in THF (2 mL) and the resulting mixture was stirred for 45 min. at room temp. The reaction mixture was concentrated to dryness under reduced pressure and the residue was co-evaporated with toluene (2×10 mL). Compound 12 was recovered as a white solid (290 mg, 0.81) from the residue by column chromatography [0-5% (v/v) MeOH in $CH_2Cl_2$] $_1$H NMR (300 MHz, $CDCl_3$) d=7.47 (s, 1H), 6.06 (d, J=6.4 Hz, 1H), 5.42 (t, J=6.1 Hz, 1H), 5.31 (s, 0.4H), 4.93 (dd, J=3.5, 5.6 Hz, 1H), 4.31 (d, J=2.5 Hz, 1H), 4.01-3.82 (m, 2H), 2.08 (s, 3H), 1.92 (s, 3H), 1.88 (s, 6H)

Example 4. Triphosphate Synthesis (Ludwig-Eckstein) (FIG. 7)

To a solution of compound 12 (0.290 g, 0.82 mmol) in pyridine (3 mL) and dioxane (6 mL) was added a solution of 2-chloro-4-H-1,3,2-benzodioxaphosphorin-4-one (0.250 g, 1.23 mmol) in dioxane (6.0 mL) at room temperature. After incubation for 15 min, a mixture of tributylammonium pyrophosphate in DMF (0.8 g in 1.9 mL of DMF, 1.5 mmol) and tributylamine (0.7 mL) was added. After incubating for 20 min, a solution of iodine (0.332 g, 1.3 mmol) and water (162.5 µL) in pyridine (8 mL) was added. After incubating for 30 min, the reaction was quenched by the addition of aqueous $Na_2SO_3$ (5%, until color disappears). The pyridine and dioxane were removed by rotary evaporation. The residue was dissolved in a mixture of water and acetonitrile (10 mL each) and kept at room temperature overnight. The product was resolved by reverse phase preparative LC (gradient 25 mM TEAA to 25 mM TEAA: $CH_3CN$ (1:1) =5:95 in 38 min, running time 46 min), with the solvents in the fraction containing the product removed by lyophilization. The residue was dissolved in ammonium hydroxide (2 mL), and the solution was stirred at room temperature for 3 h. The solution was injected onto an ion exchange HPLC column.

The triphosphate product 13 (15 µmole) was recovered as a yellow solid by lyophilization of fractions collected by gradient elution (water to 1 M ammonium bicarbonate over 32 min; running time 42 min). $^{31}$P NMR of the compound showed the presence of the product peaks. It was purified again by reverse phase preparative LC (gradient 50 mM TEAB to 50 mM TEAB: CH$_3$CN (1:1)=5:95 in 38 min, running time 46 min), with the solvents in the fraction containing the product removed by lyophilization.

Synthesis of 14 (FIG. 7)

Cleavage rTTP-ONH$_2$ Oxime with buffered methoxyamine pH=5.5 The buffered MeONH$_2$·HCl solution was prepared by diluting 3.1 M MeONH$_2$·HCl (1 mL) solution with 1M NH$_4$CO$_3$ (2.7 mL). The pH of the resulting solution was measured with a paper strip to be 6. Terminator oxime (0.2 µmol) is lyophilized in an Eppendorf tube with a screw cap. Add buffered MeONH$_2$ solution (0.8 mL) vortexed. Incubated at room temperature for 4 h, then neutralize by addition of more 1M NH$_4$CO$_3$ (0.8 mL) and lypholized. The lypholized sample were dissolved in H$_2$O (0.5 mL). The product was resolved by ion exchange preparative LC (gradient H$_2$O to 1M ammonium bicarbonate in 40 min, running time 46 min), with the solvents in the fraction containing the product removed by lyophilization.

Synthesis of RNA Aminoxy Analog of Azido A

Synthesis of Compound 15 (FIG. 9)

Compound 10 (9.1 g, 17.3 mmol) and 6-chloropurine (2.7 g, 17.3 mmol) are added under stirring to anhydrous MeCN (50 mL) containing molecular sieves (MS 4 A) under argon. The solution is cooled to 0° C. and TMSOTf (2.7 mL, 13.8 mmol) is added dropwise to this solution. The reaction mixture is then heated to 60° C. in an oil bath and the temperature is maintained for 18 h. The progress of the reaction is monitored by TLC, and the reaction is quenched when completed by addition of triethylamine to pH 7. The solvent is then removed, and the material is recovered by column chromatography (methanol:dichloromethane, 1:20) to give a yellowish solid.

Synthesis of Compound 16 (FIG. 9)

Lithium azide (7.5 g, 152 mmol) is added to a stirred solution of compound 15 (8.5 g, 13.8 mmol) in dry DMF. The mixture is stirred at room temperature for 60 h, and then the solvents are removed under vacuum. The crude product is recovered by column chromatography (methanol:dichloromethane, 1:20) to obtain the product as a white solid.

Synthesis of Compound 17 (FIG. 9)

Tetrabutylammonium fluoride (1.42 mL, 1.4 mmol, 1.0 m solution in THF) is added to a solution of 11 (741 mg, 1.18 mmol) in THF (2 mL). The resulting mixture is stirred for 45 min. at r.t. The reaction mixture is then concentrated to dryness under reduced pressure and the residue is co-evaporated with toluene (2×10 mL). The crude product is recovered by column chromatography [0-5% (v/v) MeOH in CH$_2$Cl$_2$] to give compound 17 as a white solid.

Synthesis of Compound 18 Triphosphate Synthesis (Ludwig-Eckstein) (FIG. 9)

A solution of 2-chloro-4-H-1,3,2-benzodioxaphosphorin-4-one (0.250 g, 1.23 mmol) in dioxane (6.0 mL) is added to a solution of compound 17 (0.315 g, 0.81 mmol) in pyridine (3 mL) and dioxane (6 mL). After incubation for 15 min, a mixture of tributylammonium pyrophosphate in DMF (0.8 g in 1.9 mL of DMF, 1.5 mmol) and tributylamine (0.7 mL) is added to the reaction solution. After the reaction mixture is incubated for another 20 min, a solution of iodine (0.332 g, 1.3 mmol) and water (162.5 µL) in pyridine (8 mL) is added. The mixture is incubated for 30 min, and then quenched by the addition of aqueous Na$_2$SO$_3$ (5%, until color disappears). The solvents pyridine and dioxane are removed by rotary evaporation. The residue is then dissolved in a mixture of water and acetonitrile (10 mL each) and stored at room temperature overnight. The product is recovered by reverse phase preparative LC (gradient 25 mM TEAA to 25 mM TEAA: CH$_3$CN (1:1)=5:95 in 38 min, running time 46 min), with the solvents in the fraction containing the product removed by lyophilization. The residue obtained after lyophilization is treated with ammonium hydroxide (2 mL), and the solution is stirred at room temperature for 3 hours. The ammonia is removed by rotary evaporation and the crude product is isolated by ion exchange HPLC.

The triphosphate product 18 is recovered as a solid by lyophilization of fractions collected by gradient elution (water to 1 M ammonium bicarbonate over 32 min; running time 42 min). $^{31}$P NMR is used to analyze the product, which may then be further purified by reverse phase preparative LC (gradient 50 mM TEAB to 50 mM TEAB: CH$_3$CN (1:1)=5:95 in 38 min, running time 46 min), with the solvents in the fraction containing the product removed by lyophilization.

Synthesis of 19 (FIG. 9)

Cleavage of Oxime with Buffered Methoxyamine pH=5.5
A buffered McONH$_2$·HCl solution is prepared by diluting 3.1 M MeONH$_2$·HCl (1 mL) solution with 1 M NH$_4$CO$_3$ (2.7 mL). The pH of the resulting solution is measured using a pH strip to be 6. The buffered MeONH$_2$ solution (0.8 mL) is added to a lyophilized vial of compound 18 (0.2 µmol) and the solution is vortexed. The mixture is incubated at room temperature for 4 h, and then neutralized by addition of more 1 M NH$_4$CO$_3$ (0.8 mL). The solvents are removed by lyophilization. The lyophilized sample is dissolved in H$_2$O (0.5 mL), and the crude product is isolated using ion exchange preparative LC (gradient H$_2$O to 1 M ammonium bicarbonate in 40 min, running time 46 min), with the solvents in the fraction containing the product removed by lyophilization to give 19.

Synthesis of RNA Aminoxy Analog of Azido G (FIG. 11)

Synthesis of Compound 2 (FIG. 11)

DMAP (122 mg, 1 mmol, 0.2 equiv), triethylamine (3 mL, 20 mmol, 4 equiv) and 2,4,6-tri-isopropylbenzenesulfonyl chloride (5 g, 16 mmol, 3 equiv) are all added to a solution of 1 (3.1 g, 5 mmol, 1 equiv) in 30 mL of anhydrous dichloromethane. After 2 h of stirring at r.t., the mixture is diluted with 100 mL of ethyl acetate, washed three times with saturated bicarbonate solution, and washed three times with brine. The organic layers are combined, dried over Na$_2$SO$_4$ and evaporated to dryness. The desired compound is recovered from the resulting oil by column chromatography (isocratic cyclohexane/ethyl acetate, 7:3 (v/v)) to yield pure compound 2 is obtained as a yellow foam.

Synthesis of Compound 3 (FIG. 11)

DABCO (1.2 g, 10.6 mmol, 2 equiv) and 3 g of dry 3 Å molecular sieves are added to a solution of 2 (4.32 g, 4.8 mmol, 1 equiv) in anhydrous dioxane (80 mL). After 30 min of stirring at r.t., 2-(trimethylsilyl)ethanol (4 mL, 26.6 mmol, 5 equiv) and DBU (2 mL, 13.8 mmol, 2.5 equiv) are added to the reaction mixture. Mixture is stirred overnight under argon, and then filtered off to remove insoluble impurities. Filtrate is then diluted with 250 mL of ethyl acetate and washed three times with brine. Organic layers are combined together, dried over $Na_2SO_4$ and evaporated to dryness. Product 3 is used in next step without further purification.

Synthesis of Compound 4 (FIG. 11)

A solution of 3 (4.8 g, 6.7 mmol) in $CH_2Cl_2$ (300 mL) is cooled to −78° C. To this stirred solution of 3 is added TMS-N3 (8.8 mL, 67 mmol) followed by dropwise addition of t-BuONO (8 mL, 67 mmol). The reaction mixture is allowed to warm to r.t. and stirred for 9 h. 1:1 $H_2O$/MeOH (100 mL) is added to the reaction mixture and the stirring is continued for 1 h. The mixture is then extracted with $CH_2Cl_2$. After layer separation, the organic layer is removed, washed with water, dried over $Na_2SO_4$, and evaporated to dryness. The crude product is purified on silica gel column using 10% EtOAc/hexanes to afford 4 as white, foamy solid.

Synthesis of Compound 5 (FIG. 11)

TBAF (52 mL, 52 mmol, 1.0 M solution in THF) is added to a solution of 4 (4.8 mmol, 1 equiv) in THF (25 mL). Stir the resulting mixture for 45 min. at r.t. Concentrate the reaction mixture to dryness under reduced pressure and the residue was co-evaporated with toluene (2×50 mL). Purify the crude product by column chromatography [0-5% (v/v) MeOH in $CH_2Cl_2$] to give compound 5 as a white solid.

Synthesis of Compound 6 Triphosphate Synthesis (Ludwig-Eckstein) (FIG. 11)

Compound 5 (0.328 g, 0.81 mmol) in pyridine (3 mL) and dioxane (6 mL) is added to a solution of 2-chloro-4-H-1,3,2-benzodioxaphosphorin-4-one (0.250 g, 1.23 mmol) in dioxane (6.0 mL). After incubation for 15 min, a mixture of tributylammonium pyrophosphate in DMF (0.8 g in 1.9 mL of DMF, 1.5 mmol) and tributylamine (0.7 mL) is added to the reaction solution. After incubating the reaction for another 20 min, a solution of iodine (0.332 g, 1.3 mmol) and water (162.5 μL) in pyridine (8 mL) is added to the reaction. Incubate the reaction for 30 min, then quench it by the addition of aqueous $Na_2SO_3$ (5%, until color disappears). Remove pyridine and dioxane by rotary evaporation. Dissolve the residue in a mixture of water and acetonitrile (10 mL each) and keep it at room temperature overnight. Resolve the product by reverse phase preparative LC (gradient 25 mM TEAA to 25 mM TEAA: $CH_3CN$ (1:1)=5:95 in 38 min, running time 46 min), with the solvents in the fraction containing the product removed by lyophilization. Dissolve the residue obtained after purification in ammonium hydroxide (2 mL), and stir the solution at room temperature for 3 h. Ammonia in the solution is removed using rotavap and the crude product is purified by ion exchange HPLC.

The triphosphate product 6 is recovered as a solid by lyophilization of fractions collected by gradient elution (water to 1 M ammonium bicarbonate over 32 min; running time 42 min). $^{31}P$ NMR of the compound showed the presence of the product peaks. It was purified again by reverse phase preparative LC (gradient 50 mM TEAB to 50 mM TEAB: $CH_3CN$ (1:1)=5:95 in 38 min, running time 46 min), with the solvents in the fraction containing the product removed by lyophilization.

Synthesis of 7 (FIG. 11)

Cleavage Oxime with Buffered Methoxyamine pH=5.5

A buffered $MeONH_2$·HCl solution is prepared by diluting 3.1 M $MeONH_2$·HCl (1 mL) solution with 1 M $NH_4CO_3$ (2.7 mL). The pH of the resulting solution is measured using a pH strip to be 6. The buffered $MeONH_2$ solution (0.8 mL) is added to a lyophilized vial of compound 6 (0.2 μmol) and the mixture is vortexed and then incubated at room temperature for 4 h. The pH is then neutralized by addition of more 1M $NH_4CO_3$ (0.8 mL) and the mixture is lyophilized. The residue is dissolved in $H_2O$ (0.5 mL) and the crude product is isolated using ion exchange preparative LC (gradient $H_2O$ to 1M ammonium bicarbonate in 40 min, running time 46 min). The solvents in the fractions containing the product are removed by lyophilization to give 7.

Synthesis of RNA Aminoxy Analog of Azido C (FIG. 10)

Synthesis of Compound 2 (FIG. 10)

A solution of 1 (3.8 g, 6.7 mmol) in $CH_2Cl_2$ (300 mL) is cooled to −78° C. To this stirred solution TMS-N3 (8.8 mL, 67 mmol) is added followed by dropwise addition of t-BuONO (8 mL, 67 mmol). The reaction mixture is allowed to warm to r.t. and stirring is continued for 9 h. A 1:1 $H_2O$/MeOH (100 mL) mixture is added to the reaction mixture and the stirring is continued for a further 1 h. The mixture is then extracted with $CH_2Cl_2$. After layer separation, the organic layer is removed, washed with water, dried over $Na_2SO_4$, and evaporated to dryness. The crude product is recovered by silica gel column using 10% EtOAc/hexanes to afford 2 as white, foamy solid.

Synthesis of Compound 3 (FIG. 10)

TBAF (26 mL, 26 mmol, 1.0 M solution in THF) is added to a solution of 2 (2.4 mmol, 1 equiv.) in THF (25 mL). Stir the resulting mixture for 45 min. at r.t. Concentrate the reaction mixture to dryness under reduced pressure and the residue was co-evaporated with toluene (2×50 mL). Purify the crude product by column chromatography [0-5% (v/v) MeOH in $CH_2Cl_2$] to give compound 3 as a white solid.

Synthesis of Compound 4 Triphosphate Synthesis (Ludwig-Eckstein) (FIG. 10)

2-Chloro-4-H-1,3,2-benzodioxaphosphorin-4-one (0.250 g, 1.23 mmol) in dioxane (6.0 mL) is added to a solution of compound 3 (0.296 g, 0.81 mmol) in pyridine (3 mL) and dioxane (6 mL). After incubation for 15 min, a mixture of tributylammonium pyrophosphate in DMF (0.8 g in 1.9 mL of DMF, 1.5 mmol) and tributylamine (0.7 mL) is added to the reaction solution. After incubating the reaction for another 20 min, a solution of iodine (0.332 g, 1.3 mmol) and water (162.5 µL) in pyridine (8 mL) is added to the reaction. Incubate the reaction for 30 min, then quench it by the addition of aqueous Na$_2$SO$_3$ (5%, until color disappears). Remove pyridine and dioxane by rotary evaporation. Dissolve the residue in a mixture of water and acetonitrile (10 mL each) and keep it at room temperature overnight. Resolve the product by reverse phase preparative LC (gradient 25 mM TEAA to 25 mM TEAA: CH$_3$CN (1:1)=5:95 in 38 min, running time 46 min), with the solvents in the fraction containing the product removed by lyophilization. Dissolve the residue obtained after purification in ammonium hydroxide (2 mL), and stir the solution at room temperature for 3 h. Ammonia in the solution is removed using rotavap and the crude product is purified by ion exchange HPLC.

The triphosphate product 4 is recovered as a solid by lyophilization of fractions collected by gradient elution (water to 1 M ammonium bicarbonate over 32 min; running time 42 min). $^{31}$P NMR of the compound showed the presence of the product peaks. It was purified again by reverse phase preparative LC (gradient 50 mM TEAB to 50 mM TEAB: CH$_3$CN (1:1)=5:95 in 38 min, running time 46 min), with the solvents in the fraction containing the product removed by lyophilization.

Synthesis of 5 (FIG. 10)

Cleavage Oxime with Buffered Methoxyamine pH=5.5

A buffered MeONH$_2$·HCl solution is prepared by diluting 3.1 M MeONH$_2$·HCl (1 mL) solution with 1 M NH$_4$CO$_3$ (2.7 mL). The pH of the resulting solution is measured using a pH strip to be 6. The buffered MeONH$_2$ solution (0.8 mL) is added to a lyophilized vial of compound 4 (0.2 µmol) and the solution is vortexed. The mixture is incubated at room temperature for 4 h, and the pHs then neutralized by addition of more 1M NH$_4$CO$_3$ (0.8 mL). The solvents are removed by lyophilization. The residue is dissolved in H$_2$O (0.5 mL) and the crude product is recovered using ion exchange preparative LC (gradient H$_2$O to 1M ammonium bicarbonate in 40 min, running time 46 min). The solvents in the fraction containing the product are removed by lyophilization to give 5.

What is claimed is:

1. A compound having the structure:

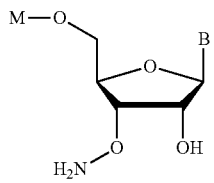

or one of its salts, wherein B is a heterocycle selected from the group consisting of

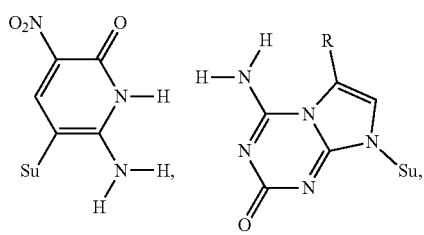

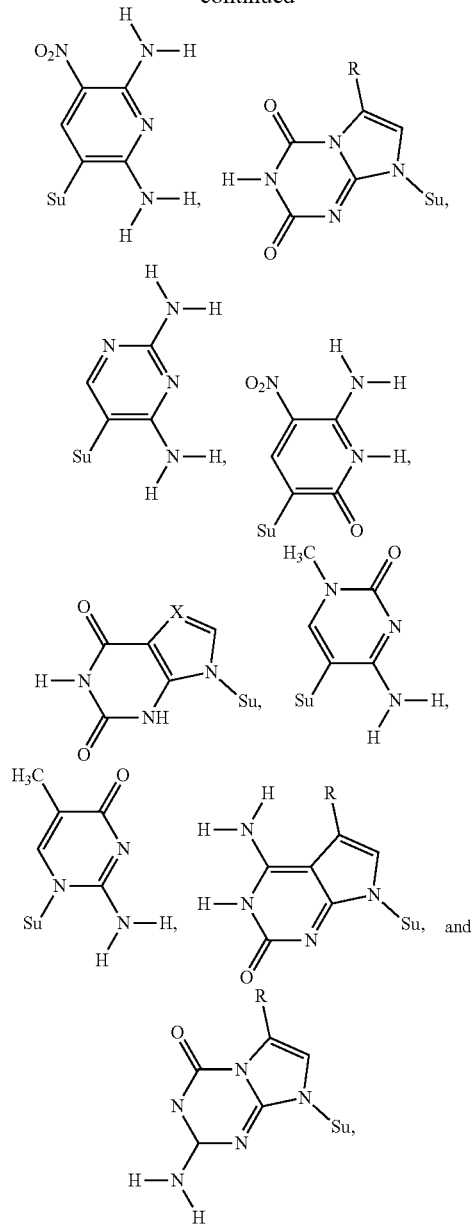

wherein Su indicates the point of attachment of the heterocycle to the sugar, R is either H, CH$_3$, or a functionalized side chain, X is either N or C—R, and M is selected from the group consisting of hydrogen, monophosphate, diphosphates, or triphosphate.

2. A composition that comprises an aqueous solution containing a compound having the structure:

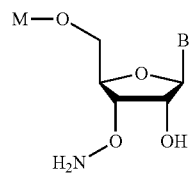

or one of its salts, wherein B is a heterocycle selected from the group consisting of

17

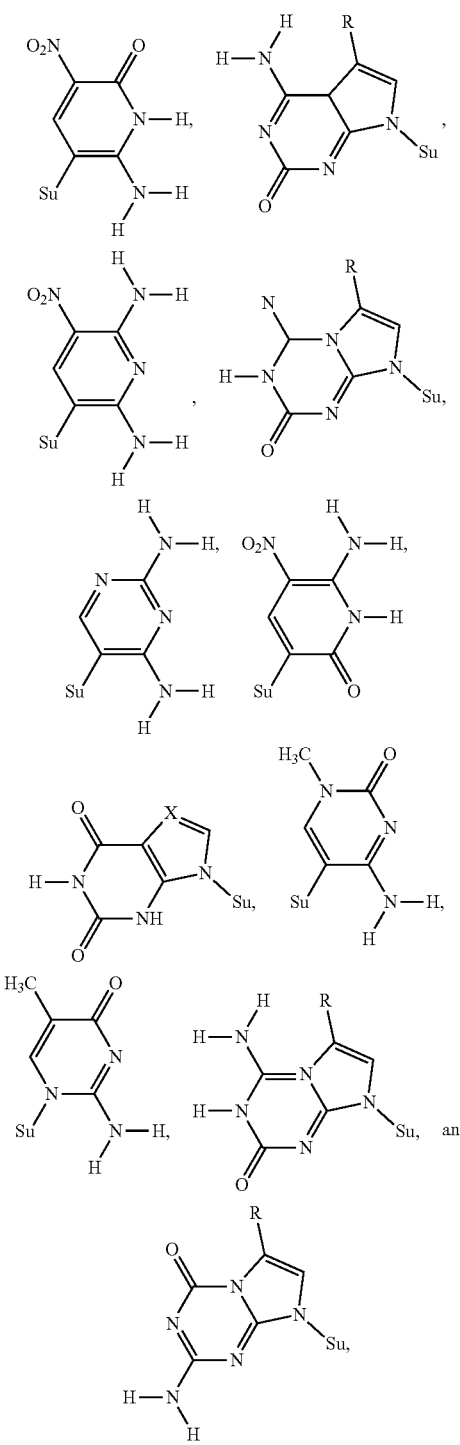

wherein Su indicates the point of attachment of the heterocycle to the sugar, R is either H, CH₃, or a functionalized side chain, X is either N or C—R, and M is selected from the group consisting of hydrogen, monophosphate, diphosphates, or triphosphate.

3. The composition of claim 2, wherein said aqueous solution is buffered.

4. The composition of claim 2, wherein said aqueous solution also contains an enzyme.

18

5. The composition of claim 4, wherein said enzyme is a DNA polymerase, and RNA polymerase, a reverse transcriptase, or a terminal transferase.

6. A process for adding to a primer a nucleotide analog, said process comprising contacting said primer in an aqueous solution containing an enzyme and a triphosphate having the structure:

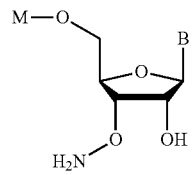

or one of its salts, wherein B is a heterocycle selected from the group consisting of

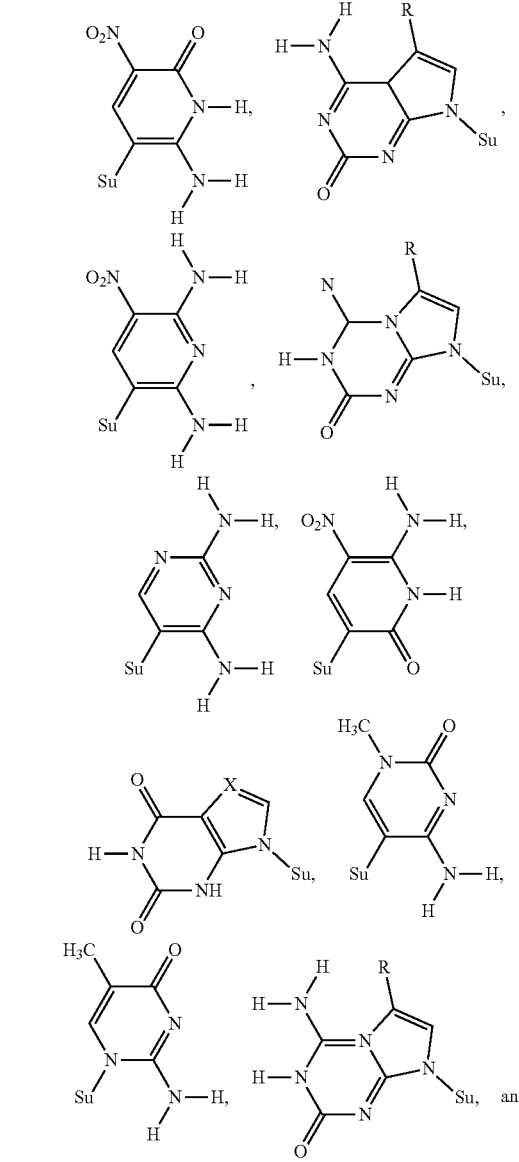

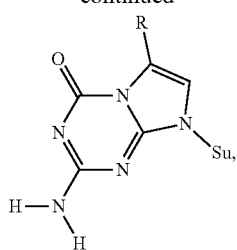

wherein Su indicates the point of attachment of the heterocycle to the sugar, R is either H, CH₃, or a functionalized side chain, X is either N or C—R, and M is triphosphate.

7. The process of claim 6, wherein said enzyme is a DNA polymerase, and RNA polymerase, a reverse transcriptase, or a terminal transferase.

8. A compound having the structure:

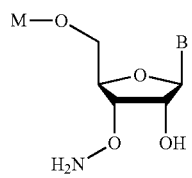

or one of its salts, wherein B is a heterocycle selected from the group consisting of

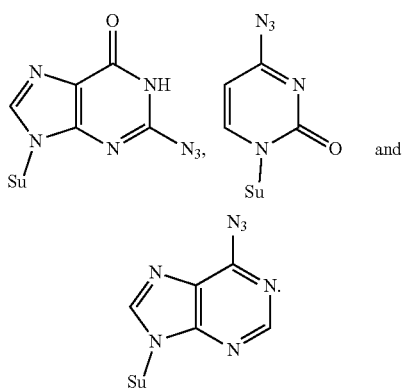

9. The compound of claim 8, wherein said B heterocycle is selected from the group consisting of

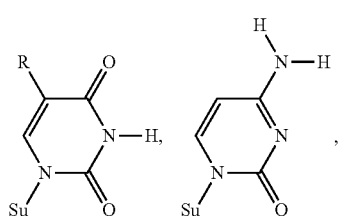

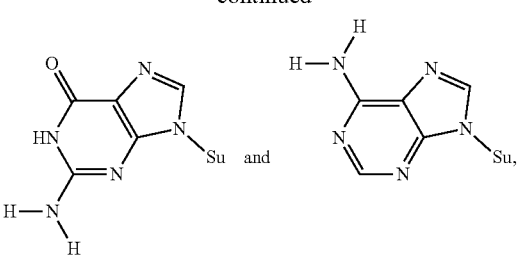

and R is either H or CH₃.

10. A compound having the structure:

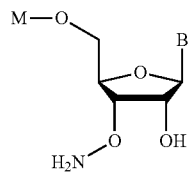

or one of its salts, wherein B is a heterocycle selected from the group consisting of

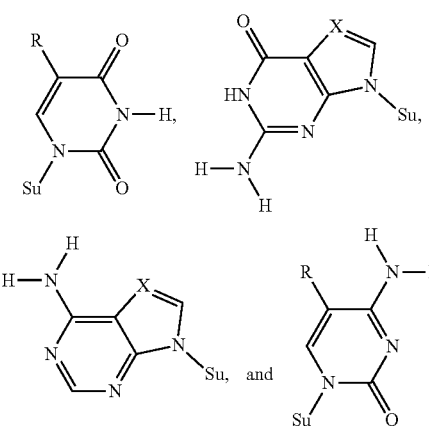

wherein Su indicates the point of attachment of the heterocycle to the sugar, R is either H, CH₃, or a functionalized side chain, X is either N or C—R, and M is selected from the group consisting of hydrogen, monophosphate, diphosphates, or triphosphate.

11. The compound of claim 10, wherein said B heterocycle is selected from the group consisting of

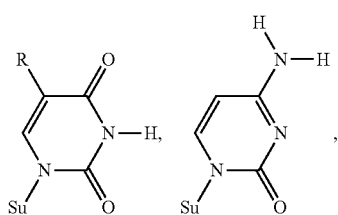

-continued

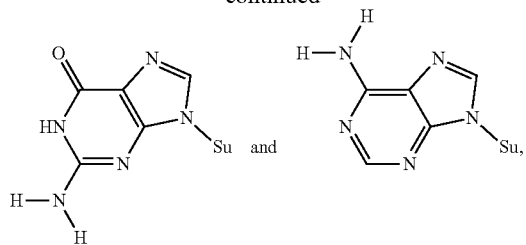

and R is either H or CH$_3$.

12. The compound of claim 11, wherein said B heterocycle is either thymine or uracil.

13. A composition that comprises an aqueous solution containing a compound having the structure:

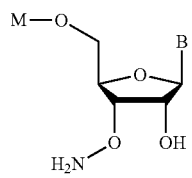

or one of its salts, wherein B is a heterocycle selected from the group consisting of

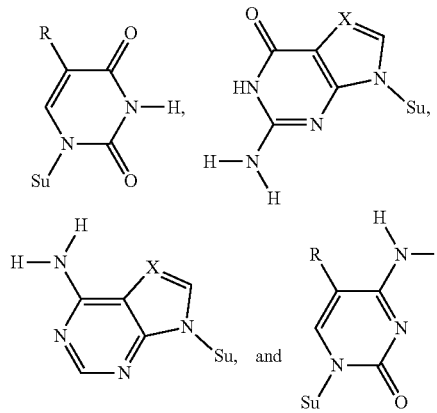

wherein Su indicates the point of attachment of the heterocycle to the sugar, R is either H, CH$_3$, or a functionalized side chain, X is either N or C—R, and M is selected from the group consisting of hydrogen, monophosphate, diphosphates, or triphosphate.

14. The composition of claim 13, wherein said B heterocycle is selected from the group consisting of

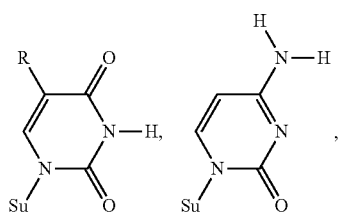

-continued

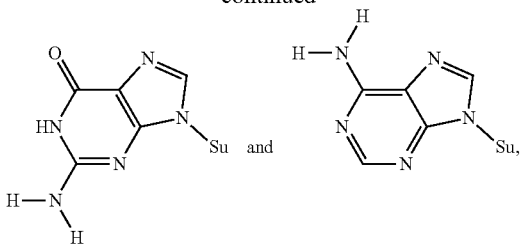

and R is either H or CH$_3$.

15. The composition of claim 13 or claim 14, wherein said aqueous solution is buffered.

16. The composition of claim 13 or claim 14, wherein said aqueous solution also contains an enzyme.

17. The composition of claim 16, wherein said enzyme is a DNA polymerase, and RNA polymerase, a reverse transcriptase, or a terminal transferase.

18. A process for adding to a primer a nucleotide analog, said process comprising contacting said primer in an aqueous solution containing an enzyme and a triphosphate having the structure:

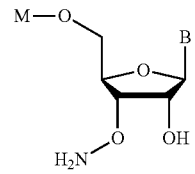

or one of its salts, wherein B is a heterocycle selected from the group consisting of

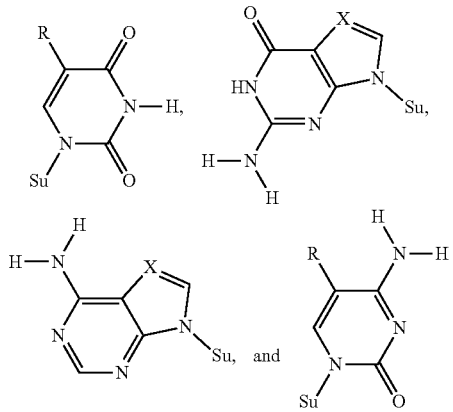

wherein Su indicates the point of attachment of the heterocycle to the sugar, R is either H, CH$_3$, or a functionalized side chain, X is either N or C—R, and M is triphosphate.

19. The process of claim 18, wherein said enzyme is a DNA polymerase, and RNA polymerase, a reverse transcriptase, or a terminal transferase.

* * * * *